(12) United States Patent  (10) Patent No.: US 7,901,707 B2
Allen et al.  (45) Date of Patent: Mar. 8, 2011

(54) BIODEGRADABLE BIOCOMPATIBLE IMPLANT AND METHOD OF MANUFACTURING SAME

(76) Inventors: Christine Allen, Toronto (CA); Justin Grant, Toronto (CA); Micheline Piquette-Miller, Toronto (CA)

( * ) Notice: Subject to any disclaimer, the term of this patent is extended or adjusted under 35 U.S.C. 154(b) by 457 days.

(21) Appl. No.: 11/079,116

(22) Filed: Mar. 15, 2005

(65) Prior Publication Data

US 2005/0208122 A1    Sep. 22, 2005

(51) Int. Cl.
A61F 13/00 (2006.01)
A61K 31/722 (2006.01)

(52) U.S. Cl. .............................. 424/443; 514/55; 514/78

(58) Field of Classification Search .................. 424/443; 514/55, 78
See application file for complete search history.

(56) References Cited

U.S. PATENT DOCUMENTS

| | | | | |
|---|---|---|---|---|
| 5,843,509 | A * | 12/1998 | Calvo Salve et al. | 424/489 |
| 6,521,211 | B1 * | 2/2003 | Unger et al. | 424/9.52 |
| 6,685,917 | B2 * | 2/2004 | Rosenthal et al. | 424/49 |
| 6,730,735 | B2 * | 5/2004 | Davis et al. | 525/54.2 |
| 2002/0192280 | A1 * | 12/2002 | Hunter et al. | 424/465 |
| 2003/0113379 | A1 * | 6/2003 | Chen et al. | 424/486 |
| 2004/0076582 | A1 * | 4/2004 | Dimatteo et al. | 424/1.49 |
| 2004/0077629 | A1 * | 4/2004 | Brown | 514/214.03 |
| 2004/0142857 | A1 * | 7/2004 | Gallop et al. | 514/8 |
| 2008/0262286 | A1 * | 10/2008 | Hallahan et al. | 600/1 |

OTHER PUBLICATIONS

Takeuchi et al, Chem. Pharm. Bull, vol. 42 (9), pp. 1954-1956, 1994.*
Henriksen et al Int. J. Pharm. vol. 146, pp. 193-204 (1997).*

* cited by examiner

*Primary Examiner* — Gollamudi S Kishore
(74) *Attorney, Agent, or Firm* — Eduardo Krupnik

(57) ABSTRACT

Formulations or delivery systems are provided for controlled release of therapeutically active agents. The delivery systems are composed of polymer and lipid materials and may be prepared as a gel, paste, solution, film, implant or barrier depending on the intended application. The polymer component of the matrix is the naturally occurring biomaterial, chitosan, or a mixture of chitin and chitosan. The lipid component may include phosphatidylcholine, phosphatidylserine, phosphatidylinositol, phosphatidyl or a mixture thereof. The delivery system may be used for delivery of hydrophilic agents, hydrophobic agents or combinations thereof. The therapeutically active agents may be formulated within the matrix as free agents or incorporated into particles. In a preferred embodiment the agents are incorporated into polymeric particles that are dispersed throughout the matrix.

33 Claims, 23 Drawing Sheets

Low Drug: Matrix PTX-PoLi Implant. Daily PTX dose provided from PTX PoLi delivery system implanted *in vivo* into peritoneal cavity of CD-1 mice. Data reported as mean ± standard deviation. An average of 8.5 ± 2.6 mg/kg/day was provided.

(a)                                                                 (b)

Figure 7
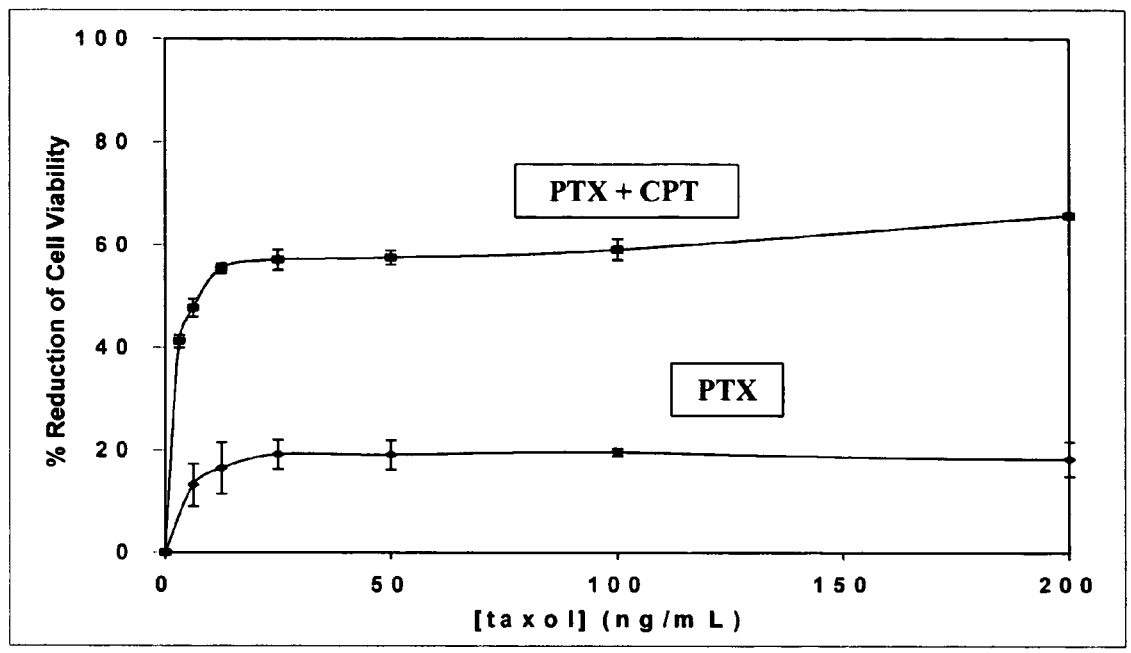
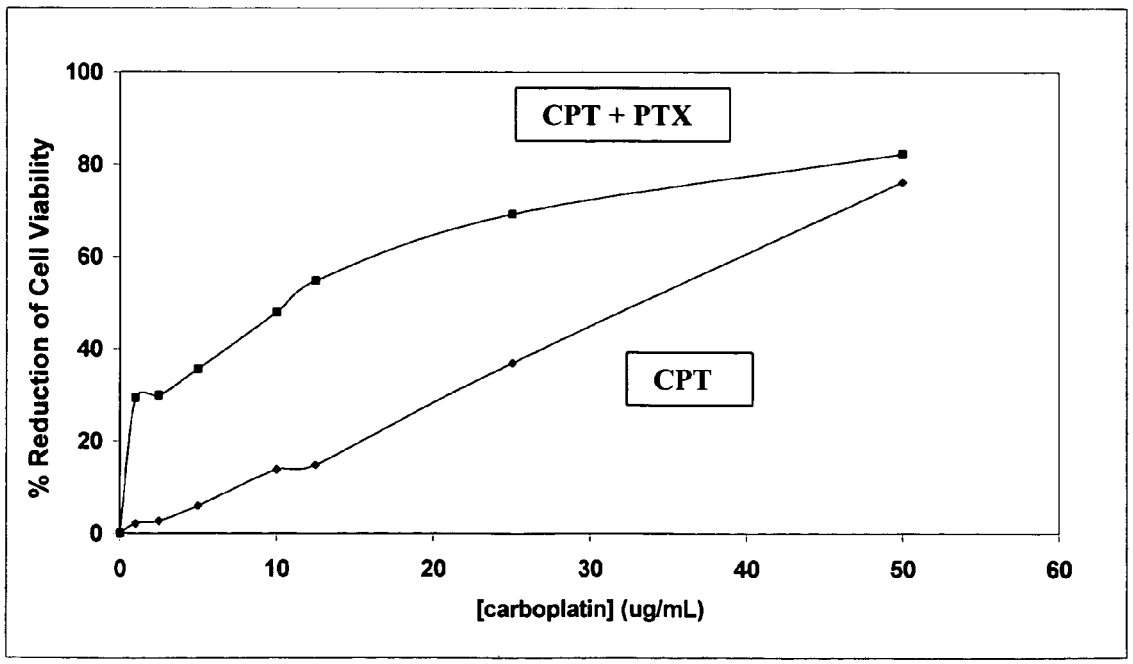

Figure 10
(a) 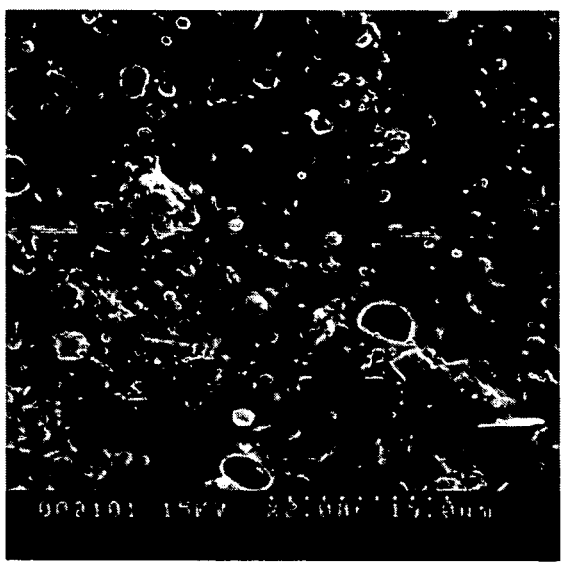 (b) 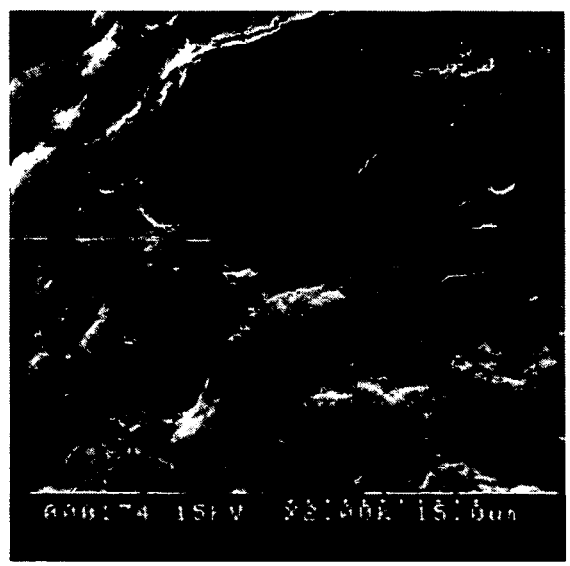

Figure 11

| FILM COMPOSITION | RATIO (wt:wt) | MAXIMUM SWELLING RATIO ($Q_M$) |
|---|---|---|
| 1% Chitosan | | *** |
| 2% Chitosan | | *** |
| Chitosan : DMPE | 1 : 0.1 | *** |
| Chitosan : DPPC | 1 : 0.1 | *** |
| Chitosan : DMPG | 1 : 0.1 | 43.8± 38.4 |
| Chitosan : DMPC | 1 : 0.1 | 17.1± 0.9 |
| Chitosan : pure ePC | 1 : 0.2 | 5.3± 0.6 |
| Chitosan : pure ePC | 1 : 0.4 | 2.7± 0.2 |
| Chitosan : pure ePC | 1 : 0.8 | 2.6± 0.7 |
| Chitosan : pure ePC | 1 : 1.7 | 1.5± 0.0 |
| Chitosan : pure ePC | 1 : 2.5 | 1.3± 0.0 |
| Chitosan : crude ePC | 1 : 0.1 | 5.9± 0.8 |
| Chitosan : crude ePC | 1 : 0.2 | 4.8± 0.1 |
| Chitosan : crude ePC | 1 : 0.4 | 3.1± 0.4 |
| Chitosan : crude ePC | 1 : 0.8 | 3.2± 0.2 |
| Chitosan : crude ePC | 1 : 1.7 | 1.7± 0.1 |
| Chitosan : crude ePC | 1 : 2.5 | 1.6± 0.0 |

Maximum Swelling Ratios (Qm) of films (n=3) with different material compositions in 0.01M PBS for 24 hours. 2% chitosan was used for all formulations, unless indicated otherwise. (*** Film swelled rapidly and could not be weighed).

Figure 12

| Drug | SKOV3 cells | | CAOV3 cells | |
|---|---|---|---|---|
| Paclitaxel (PTX) | | | | |
| 24 hr | > 200 ng.mL | > 235 nM | > 200 ng/mL | > 235 nM |
| 48 hr | > 200 ng/mL | > 235 nM | > 200 ng.mL | > 235 nM |
| 72 hr | 21.8 ng/mL | 25.5 nM | 30.2 ng/mL | 35.4 nM |
| Carboplatin (CPT) | | | | |
| 24 hr | 62.3 µg/mL | 167 µM | 54.9 µg/mL | 147.9 µM |
| 48 hr | 33.3 µg/mL | 89.7 µM | 15.8 µg/mL | 42.6 µM |
| 72 hr | 26.0 µg/mL | 70.0 µM | 5.1 µg/mL | 13.7 µM |

Impact of sustained exposure on chemosensivity of ovarian cancer cells to PTX and CPT (expressed as $IC_{50}$ values).

Low Drug: Matrix PTX-PoLi Implant. Daily PTX dose provided from PTX PoLi delivery system implanted *in vivo* into peritoneal cavity of CD-1 mice. Data reported as mean ± standard deviation. An average of 8.5 ± 2.6 mg/kg/day was provided.

High Drug: Matrix PTX: PoLi Implant. Daily PTX Dose provided from PTX PoLi delivery system implanted *in vivo* into peritoneal cavity of CD-1 mice. Data reported as mean ± standard deviation. An average of 11.0 ± 3.1 mg/kg/day was provided.

CPT-PoLi Implant. Cumulative CPT Dose Provided from CPT PoLi delivery system implanted *in vivo* into peritoneal cavity of CD-1 mice. Data reported as average values based on urinary excretion of CPT.

Figure 16

| Size of Implant (mg) | Surface Area of Implant (mm$^2$) | Amounts of PTX Released (X 10$^{-4}$ mg) | Intracellular Accumulation of PTX (X 10$^{-8}$ mg) | Amounts of PTX Remaining in Implants (μg) | Total Amounts of PTX Recovered (μg) | Total Amounts of PTX Loaded In Implant (μg) |
|---|---|---|---|---|---|---|
| 0.25 | 2.6 | 2.40 | 1.29 | 4.0 | 4.0 | 6.0 |
| 0.5 | 6.1 | 4.75 | 1.32 | 11.0 | 11.0 | 11.0 |
| 1.0 | 19.8 | 6.77 | 1.36 | 22.0 | 22.0 | 22.0 |
| 2.5 | 26.1 | 9.24 | 1.40 | 66.0 | 67.0 | 55.0 |
| 4.8 | 63.9 | 13.9 | 1.51 | 120.0 | 121.0 | 106.0 |

Distribution and release of $^{14}$C-PTX from PTX-chitosan-ePC films. As described in methods, $^{14}$C-PTX-chitosan-ePC films were incubated with SKOV-3 cells for 72 hrs. $^{14}$C-PTX levels were measured in media, cell lysates and digested implants. Data represents mean values (n=3).

a　　　　　　　　　　　　　　b

SKOV-3 cell morphology and viability after 72 hrs of incubation with (a) drug free chitosan-ePC (4.8 mg; 63.9 mm$^2$) (b) PTX-chitosan-ePC (4.8 mg; 63.9 mm$^2$). Images obtained using the Zeiss Axiovert 135 TV light microscope at 10x magnification.

Time course of cumulative amounts of $^{14}$C-PTX released into cell media from PTX-chitosan-ePC film (10 mg) incubated with SKOV-3 cells over 5 days.

Percentage of $^{14}$C-PTX released from PTX-chitosan-ePC implants of various sizes/surface areas in SKOV-3 cells after 72 hrs. Data represents the mean ± S.D. (n=3).

Intracellular accumulation of $^{14}$C-PTX within SKOV-3 cells after 72 hrs of incubation with varying sizes (2.6 – 63.9 mm$^2$) of PTX-chitosan-ePC. Data represents the mean ± S.D. (n=3).

Cell proliferation and viability of SKOV-3 cells incubated with various sizes of PTX-chitosan-ePC films for 72hrs. PTX-chitosan-ePC dose is expressed as (a) implant surface area and (b) log concentration of PTX released into media. Data represents the mean ± S.D. (n=3).

Post-mortem inspection and collection of different types of polymer films removed from animals 2 weeks after intraperitoneal implantation. (a) drug-free chitosan-ePC implant (b) drug-free PCL implant (c) drug-free PLA implant (d) PTX-chitosan-ePC implant.

Figure 23

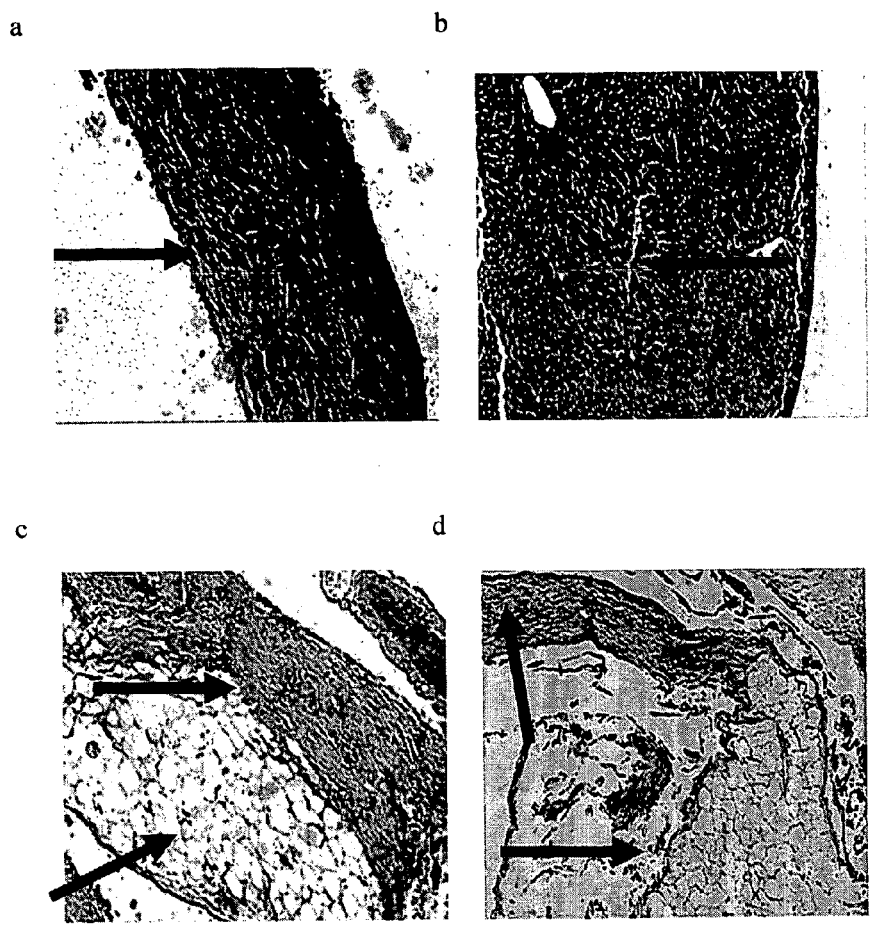

Microscopic images of paraffin fixed polymer implants (stained with hematoxylin and eosin) after 2 weeks of implantation. (a) PTX-chitosan-ePC (b) Drug-free-chitosan-ePC (c) Drug-free-PCL (d) Drug-free-PLA. Images obtained using the Zeiss Axiovert 135 TV light microscope at 5x magnification. (Black arrows depict implant, red arrows depict protein adherence and fibrous encapsulation around implant).

Figure 24

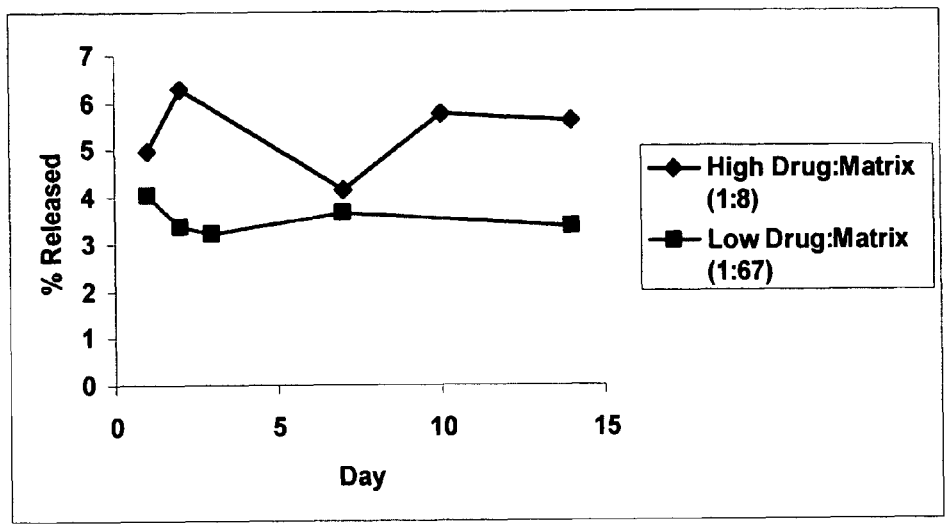

Time course of $^{14}$C-PTX released (% of total implant) *in vivo* per day from animals implanted with high drug:matrix (1:8) chitosan-ePC or low drug:matrix (1:67) chitosan-ePC over a 2 week period. Data represents the mean ± S.D. (n=3).

Figure 25

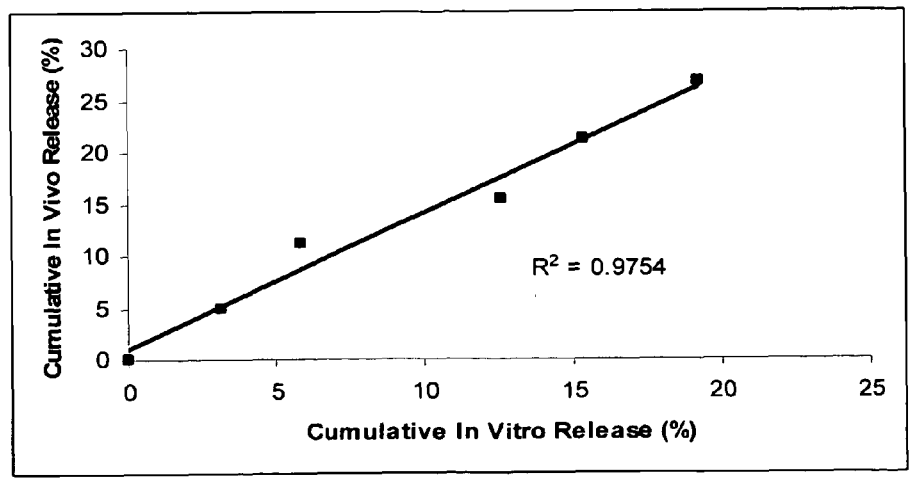

Correlation of *in vitro* and *in vivo* release of $^{14}$C-PTX from the PTX-chitosan-ePC implant system after 2 weeks. *In vitro* release was performed in RPMI 1640 cellular media containing 10% FBS.

Figure 26

|  | Implant (mg) | PTX Dosage mg/kg/week | Tumour (mg) | Tumour Burden | % Weight Gain / Loss (+/-) |
|---|---|---|---|---|---|
| control (no treatment) | 0 | 0 | 0.829 | ++++ | 10 (+) |
| control (drug free chitosan-ePC implant) | 50 | 0 | 0.209 | +++ | 8 (+) |
| PTX chitosan-ePC implant | 0.4 | 20 | 0 | - | 24 (+) |
|  | 50 | 70 | 0 | - | 19 (+) |
|  | 100 | 140 | 0 | - | 5 (+) |
| Bolus (Taxol®) | 0 | 20 | 0 | - | 8 (+) |

Animals: female CD-1 nude mice (n=3, group); Cell Line: SKOV-3; $1 \times 10^7$ cells injected PTX Chitosan-ePC Implant (sustained), Taxol ® (bolus); Treatment: commenced Day 5 post SKOV-3 inocculation; 25 day duration (implants); 1 bolus PTX injection / week for a total of 3 injections (Taxol ® )

Tumour Burden Assessment:

++++   High, several clusters of large (5-10 mm in diameter) solid tumours, easily visible in peritoneal cavity +++   Moderate, clusters of tumours (3-5 mm in diameter), readily visible, but not as extensive as High ++   Low, no apparent large tumours, but visible small foci on peritoneum, omentum, uterine fat pads, diaphragm +   Scarce, only small foci seen on peritoneum, omentum, diapragm

-   no tumour

BIODEGRADABLE BIOCOMPATIBLE IMPLANT AND METHOD OF MANUFACTURING SAME

FIELD OF THE INVENTION

This invention relates in general to a biodegradable, biocompatible implant and method of manufacturing this implant and furthermore relates to the use of this implant in the delivery of pharmaceutically active agents and more particularly the use of a chitosan based material which can be used as an implantable controlled drug delivery composition or system.

BACKGROUND OF THE INVENTION

When administered in standard intravenous or oral formulations, many pharmaceutical agents fail to reach the target organ in an effective concentration, or are not effective due to rapid elimination. This lack of effectiveness of the drug can result from a number of factors including: acid hydrolysis or incomplete absorption from the gastrointestinal tract, inability of the drug to cross physiological membranes such as the blood brain barrier, insufficient distribution to the site of action, enzymatic deactivation of the compound in the liver or blood prior to reaching the target organ, and/or rapid secretion of the drug into bile, urine or feces.

Delivery of drugs directly to the site of action using localized delivery systems provides advantages in that it provides high drug concentrations at the site of action while reducing systemic exposure. Indeed, in recent years it has been demonstrated that local administration offers increased efficacy and decreased toxicity of anti-neoplastic agents in the treatment of various cancers. Implantation of a biodegradable drug delivery device containing active drug substances could provide high local concentrations of the pharmaceutically active agent for a sustained period of time.

It is known that there is limited success in achieving cures for many prevalent diseases such as cancer, AIDS, infectious, immune or cardiovascular disorders using single therapeutic agents. Thus, combinations of therapeutic agents are generally used to combat life-threatening diseases such as AIDS and cancers. Indeed, numerous clinical trials have demonstrated enhanced efficacy and patient prognosis in cancer patients treated with combinations of anti-neoplastic agents. (Frei, et al., Clin. Cancer Res. (1998) 4:2027-2037; Todd, et al., J. Clin. Oncol. (1984) 2:986-993).

Often drug combinations demonstrate synergistic effects, with pronounced increases in total therapy efficacy. Synergistic combinations of agents have also been shown to reduce toxicity due to lower dose requirements, to reduce the development of multi-drug resistance (Shlaes, et al., Clin. Infect. Dis. (1993) 17:S527-S536) and to increase cancer cure rates (Barriere, et al., Pharmacotherapy (1992) 12:397-402; Schimpff, Support Care Cancer (1993) 1:5-18). By choosing agents which act by different mechanisms of action, multiple molecular or biochemical pathways can be averted, thus resulting in drug synergy (Shah and Schwartz, Clin. Cancer Res. (2001) 7:2168-2181).

Numerous studies have reported synergism in cancer therapy, with drug combinations exhibiting greater antineoplastic activity than the combined effects of either drug alone. Several of these include: Cisplatin and etoposide (Kanzawa, et al., Int. J. Cancer (1997) 71(3):311-319); L-canavanine and 5-fluorouracil (Swaffar, et al., Anti-Cancer Drugs (1995) 6:586-593), Vinblastine and recombinant interferon-P (Kuebler, et al., J. Interferon Res. (1990) 10:281-291); Cisplatin and carboplatin (Kobayashi, et al., Nippon Chiryo Gakkai Shi (1990) 25:2684-2692); Ethyl deshydroxy-sparsomycin and cisplatin or cytosine arabinoside (AraC) or methotrexate or 5-FU or vincristine (Hofs, et al., Anticancer Drugs (1994) 5:35-42); and Cisplatin and paclitaxel (Engblom, et al., Br. J. Cancer (1999) 79:286-292). To date, very few delivery systems have been developed for combinations of agents.

In order to achieve effective sustained concentrations of drugs at the target organs, the drug is usually combined with a carrier that is biocompatible and biodegradable. Suitable carriers for drug incorporation range in size from small molecules to macromolecules, including high molecular weight polymers. Polymer-based devices thus can be used to release a drug at a specific location at a controlled rate over a period of time. The most desirable polymeric matrix for drug delivery is one that is inexpensive, biocompatible, biodegradable, flexible and provides a uniform controlled release of the active substance in an aqueous environment. Chitosan based polymer blends are useful for controlled drug delivery because they degrade uniformly into non-toxic molecules that are non-mutagenic, non-cytotoxic, and non-inflammatory.

Chitosan is a natural, biodegradable cationic polysaccharide, which has previously been described as a promoter of wound healing (Balassa, 1972; Balassa, 1975). Chitosan is a commercially available inexpensive polymer which is mainly composed of D-glucosamine units that are generated through catalyzed N-deacetylation of chitin, a natural material extracted from fungi, the exoskeletons of shellfish and from algae. Chitosan has good viscoelastic properties with excellent tissue compatibility and biodegradability which renders it ideal for bioactive and resorbable implants. Moreover, chitin and partially-acetylated chitosan derivatives have been extensively investigated as implantable materials due to their favorable biocompatability and degradation to the simple amino acids; glucosamine and N-acetyl-glucosamine (Muzzarelli, 1999). Modified chitins and chitosans have been administered to humans in the form of dressings for wounded soft tissues and for the controlled delivery of drugs (Muzzarelli et al, 1986; 1999; Muzzarelli, 1993; 1996; Tokura and Azuma, 1992; Wada, 1995; Maekawa and Wada, 1990; Mita et al., 1989).

Chitosan based hydrogels may be designed for use as biomedical implants. The use of chitosan requires physical or chemical cross-linking in order to ensure stability in the biological milieu. Chitosan is a positively charged crystalline polymer that becomes increasingly soluble in medias of low pH (1% acetic acid solution, pH=5). The initial step in the film formation process is the dissolution of chitosan in acetic acid. In this step, chitosan becomes protonated as its amino groups on each polymer repeat unit becomes charged and associates with acetate counter-ions. During the drying process, water is driven out from the film, leaving the acetate molecule as a non-ionized salt. When the film is immersed in release buffer, ion exchange occurs, causing the film to swell rapidly. During the swelling of the film, acetic acid is released lowering the pH of the buffer and the film is quickly dissolved (Hoffman et. al, J. Control. Rel. (2001) 72:35-46).

Due to chitosans hydrophilic properties, most drug delivery applications uses "cross-linkers" in order to avoid this rapid dissolution (burst release) and provide stability (controlled drug release) in a biological milieu. Various cross-linking reagents have been used for chitosan gels. In the past, preparation of chitosan-based films used synthetic chemical cross-linking agents such as epoxy compounds and glutaraldehyde (Kawwamura et. al. Ind Eng Chem Res (1993), 32:

386-391; Rumunan-Lopez and R. Bodmeier, J. Control Rel. (1997); 44 215-225). Chemical cross-linking with aldehydes is not optimal for the encapsulation of proteins, peptides and other molecules with amino groups which can also undergo covalent cross-linkage. In addition, these synthetic cross-linking agents are highly cytotoxic, thus impairing the biocompatibility of these films (Nishi et al, Journal of Biomed Mater Res (1995); 29, 829-834).

Recently, various researchers have exploited non-covalent or physical cross-linking of chitosan polymer chains to achieve electrostatic and/or hydrogen bonding, thus increasing the stability and biocompatibility of the hydrogel. For example, negatively charged molecules such as oligonucleotides (DNA or RNA) engage in electrostatic interactions with chitosan to produce adducts that are stable for up to 15 days (Springate et al, (2003) Patent No. #20030134810). In addition, Hoffman et al. developed a physically cross-linked chitosan-glycerol film for the mucosal delivery of glycoproteins (Hoffman et. al, J. Control. Rel. (2001) 72:35-46).

The polymer-lipid or PoLi implant system is a physically cross-linked composition or system developed from natural ingredients (chitosan and lipid) and its stability can range from days to months depending on the formulation. The physical cross-linking within the PoLi implant is achieved through interactions between chitosan and phospholipid. Phospholipids such as phosphatidylcholine, phosphatidylethanolamine and phosphatidylglycerol are fat soluble entities that consist of lipophilic and hydrophilic components. These endogenous lipids are important components of cellular membranes in organisms and are involved in the solubilization of both hydrophilic and hydrophobic compounds.

In addition, due to the amphiphilic nature of the PoLi system it can be used for solubilization and delivery of both hydrophobic and hydrophilic agents. In this way, the PoLi formulation may be used for delivery of hydrophilic or hydrophobic drugs or combinations thereof.

Thus a biodegradable, biocompatible controlled drug delivery system or implant using a chitosan based material, the method of manufacturing this implant, the use of this implant in the delivery of pharmaceutically active agents is desirable.

SUMMARY OF THE INVENTION

An object of one aspect of the present invention is to provide improved compatible blends of pharmaceutically active agents within an implantable delivery vehicle as a method to provide sustained, local delivery of drug or drug combinations.

In accordance with one aspect of the present invention there is provided a drug delivery composition for sustained release or controlled release that includes a physically cross-linked matrix having at least one biodegradable polycationic polymer complexed with a molecule containing a phosphate group.

In accordance with another aspect of the present invention there is provided a controlled release drug delivery composition including at least one polycationic polymer with at least one molecule containing a phosphate group and at least one pharmaceutically active agent to provide controlled release of a first pharmaceutically active agent when administered to a mammal or patient.

The drug delivery compositions and/or systems, discussed herein provide controlled release or sustained release and/or protective formulations that comprise of a polycationic polymer such as chitosan, a molecule containing a phosphate group namely a phospholipid, and at least one pharmaceutically active agent.

The composition may also be comprised of chitosan or a mixture of chitin and chitosan. The phospholipid or lipid component may include phosphatidylcholines, phosphatidylserines, phosphatidylinositols, phosphatidylethanolamines, phosphatidylglycerols, or a mixture thereof. The source of phospholipids used in this invention is a commercially available egg yolk extraction primarily comprised of phosphatidylcholine (>60%) and other phospholipids (40%). Phosphatidylcholine is the principle membrane phospholipid found in human or animal cells and is commonly used in pharmaceutical liposome formulations.

The pharmaceutically active agents of the present invention can be any of those agents which are generally required to be frequently administered for maintaining the effective blood concentration or an effective concentration of the pharmaceutically active agent content locally. The pharmaceutically active agents of the present invention may be included as a first, second or in multiple quantities. Typical examples of such pharmaceutically active agents are as follows: anti-cancer or anti-proliferative agents—Carmustine, Methotrexate, Carboplatin, Cisplatin, Oxaliplatin, 5-Fluorouracil, 5-Fluorouridine, Cytarabine, Leuprolide acetate, Cyclophosphamide, Vinorelbine, Pilocarpine, Paclitaxel, Mitomycin, Camptothecin, Doxorubicin, Daunorubicin, and the like.

The drug delivery compositions may also comprise of additives that optimize the properties of the formulation such as: polymeric nanoparticles, liposomes as well as hydrophilic polymers (e.g. poly(ethylene glycol), dextran).

In some embodiments the polymer, the phospholipid, and pharmaceutically active agent or agents can be formulated as, a solution, gel, suspension, paste, slurry, film, slab, wrap, barrier or implant.

The compositions can further comprise at least one pharmaceutically acceptable carrier or excipient. The pharmaceutically acceptable carrier or excipient may be a polymeric carrier that provides controlled release of a first, second or multiple pharmaceutically therapeutic agents. The pharmaceutically acceptable carrier may comprise particles formed from a polymer or copolymer. The polymer may be a poly(ester), poly(carbonate) or poly(anhydride) or copolymer thereof. The pharmaceutically acceptable carrier or excipient may also be a liposome that provides controlled release of a first or second therapeutic agent. The liposomes are comprised of phospholipids and cholesterol.

The term "liposome" as used herein means vesicles comprised of one or more concentrically ordered lipid bilayers encapsulating an aqueous phase. Included in this definition are unilamellar vesicles. The term "unilamellar vesicle" as used herein means single-bilayer vesicles or substantially single-bilayer vesicles encapsulating an aqueous phase wherein the vesicle is less than 500 nm. The unilamellar vesicle is preferably a "large unilamellar vesicle (LUV)" which is a unilamellar vesicle between 500 and 50 nm, preferably 200 to 80 nm.

Conveniently the compositions can be prepared for intraperitoneal, intraarticular, intraocular, intratumoral, perivascular, subcutaneous, intracranial, intramuscular, intravenous, periophthalmic, inside the eyelid, intraoral, intranasal, intrabladder, intravaginal, intraurethral, and intrarectal. Preferably the compositions can be sized and formulated to be injected through a syringe needle though mode of administration need not be limited to injection. The subject or patient can be a mammal.

In accordance with another embodiment of the present invention there is provided methods of manufacturing a controlled release drug delivery composition comprising at least one polycationic polymer, such as chitosan, with at least one phospholipid component and at least one pharmaceutically active agent to provide controllable release of at least the pharmaceutically active agent when administered to a mammal or patient. The methods of manufacture may produce a solution, slurry, gel, paste, film, implant or the like. The methods may also further comprise incorporation of at least one pharmaceutical acceptable carrier or excipient that may further comprise at least a second pharmaceutically active agent.

Preferably the preparation of a film may include an initial step (Step (1)) of dissolving chitosan, chitin or a mixture thereof in water containing 0.5-2% w/w acetic acid. In a second step (Step (2)) lipid may be dissolved in a short-chain alcohol, i.e. ethanol, methanol, isopropyl alcohol. The Step (2) may be carried out at temperatures above the transition temperature of the lipid component having the highest phase transition(™). In a third step (Step (3)) the chitosan and lipid solutions may be mixed together by homogenizing at high speed for 5-15 minutes. The speed and period of mixing affect the final properties of the film. The film may then be left to dry at room temperature for several days. For preparation of a gel the steps may be as above but the mixture is left at room temperature in a sealed container until use.

In accordance with another embodiment of the present invention there is also provided methods of treating or inhibiting a proliferative disease comprising administering to a patient a therapeutically effective amount of a composition described above.

Advantages of the present invention are: protection of therapeutic agents from degradation; maintenance of effective concentrations of the therapeutic either locally or systemically, decrease of the frequency of administration of the therapeutic agent; decrease of the amount of therapeutics administered to patients per dose; and decrease of the toxicities or side effects that usually result following systemic administration.

BRIEF DESCRIPTION OF THE DRAWINGS

A detailed description of the preferred embodiments are provided herein below by way of example only and with reference to the following drawings, in which:

FIG. 7. Impact of combined PTX and CPT therapy on chemosensitivity of ovarian cancer cells to PTX and CPT expressed as IC50 values. A. Enhanced 48 hour chemosensitivity of ovarian cancer cells to PTX by addition of CPT (10 μg/ml). B. Enhanced 48 hour chemosensitivity of ovarian cancer cells to CPT by addition of PTX (50 μg/ml).

FIG. 10. High magnification SEM of paclitaxel loaded nanoparticles within the PoLi implant prior to (a) and following one month of implantation (b) in a CD-1 mouse.

FIG. 11. Table illustrating the Maximum Swelling Ratios (Qm) of films (n=3) with different material compositions in 0.01M PBS for 24 hours. 2% chitosan was used for all formulations, unless indicted otherwise. (*** Film swelled rapidly and could not be weighed).

FIG. 12. Table illustrating the impact of sustained exposure on chemosensitivity of ovarian cancer cells to PTX and CPT (expressed as IC50 values).

FIG. 16. A table illustrating the distribution and release of 14C-PTX from PTX-chitosan-ePC films. As described in methods, 14C-PTX-chitosan-ePC films were incubated with SKOV-3 cells for 72 hrs. 14C-PTX levels were measured in media, cell lysates and digested implants. Data represents mean values (n=3).

FIG. 23. Microscopic images of paraffin fixed polymer implants (stained with hematoxylin and eosin) after 2 weeks of implantation. (a) PTX-chitosan-ePC (b) Drug-free-chitosan-ePC (c) Drug-free-PCL (d) Drug-free-PLA. Images obtained using the Zeiss Axiovert 135 TV light microscope at 5× magnification. (Black arrows depict implant, red arrows depict protein adherence and fibrous encapsulation around implant).

FIG. 24. A chart illustrating time course of 14C-PTX released (% of total implant) in vivo per day from animals implanted with high drug:matrix (1:8) chitosan-ePC or low drug:matrix (1:67) chitosan-ePC over a 2 week period. Data represents the mean±S.D. (n=3).

FIG. 25. A chart illustrating correlation of in vitro and in vivo release of 14C-PTX from the PTX-chitosan-ePC implant system after 2 weeks. In vitro release was performed in RPMI 1640 cellular media containing 10% FBS.

FIG. 26. A chart illustrating efficacy of Chitosan e-PC drug delivery system, namely the tumour development in CD-1 mice inoculated with SKOV-3 cells and treated with PTX-Chitosan-ePC implant or controls.

Figure 1:
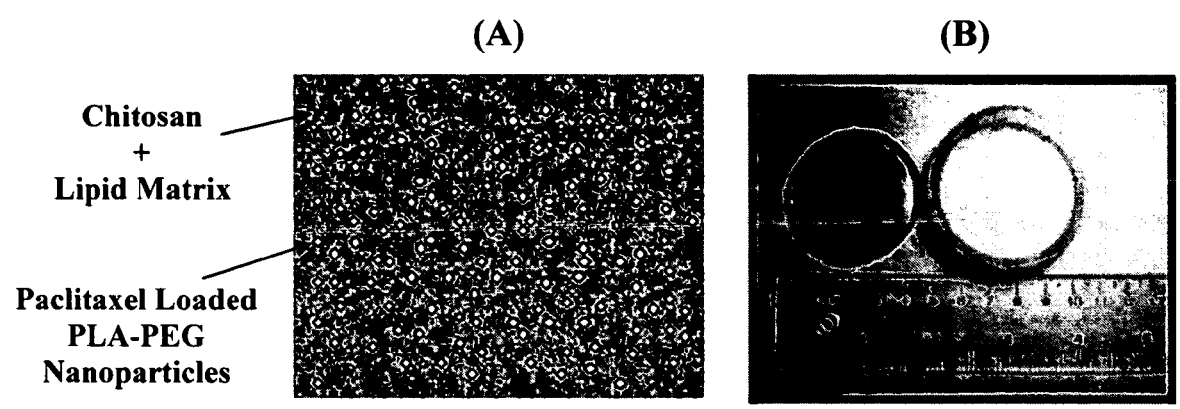
FIG. 1. A photograph and schematic of the components creating the PoLi hybrid implant system. Paclitaxel loaded PLA-PEG nanoparticles are dispersed within a chitosan and phosphatidylcholine matrix (A). Shown in (B) a photograph of the implant system (1:0.8 (w/w) chitosan to ePC) after being removed from a teflon coated dish.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Definitions

The following paragraphs provide definitions of the terms used herein. All terms used herein including those specifically discussed below in this section, are sued in accordance with their ordinary meanings unless the context or definition clearly indicates otherwise. Also unless indicated otherwise except within the claims the use of "or" includes "and" and vice-versa. Non-limiting terms are not to be construed a limiting unless expressly stated or the context clearly indicates otherwise (for example, "including", "having" and "comprising" typically indicate "including without limitation"). Singular forms including in the claims such as "a", "an" and "the" include the plural reference unless expressly stated or the context clearly indicates otherwise.

"Polymer" indicates a molecule composed of a number of repeat units.

"Chitosan" indicates any compound or composition, which is a derivative or analogue of chitin. This term also includes chitin and various derivatives of chitosan such as carboxymethylchitosan, oleoyl chitosan and pegylated chitosan (Carbomer, Inc., Westborough, Mass.) Chitosan is a linear polysaccharide composed of two monosaccharides linked by glycoside bonds and is manufactured by deacylation of chitin. Chitosan is a mucoadhesive, biocompatible polymer that is commercially available in a range of molecular weights and degrees of deacylation. As the molecule has a protonable primary amine on a side chain, chitosan has weak cationic properties. Chitosan is typically not soluble in water but may be dissolved in weak acids such as a 2% acetic acid solution, and the chitosan degrades in vivo under the action of enzymes such as lysozymes.

"Composition" as used herein should be understood to indicate a combination of multiple substances into an aggregate mixture.

"Controlled release" indicates the release of therapeutically active agents into the surrounding media or body in a selected time-dependent manner. The release can be from approximately several hours to several months.

"Drug", "therapeutic agent" "therapeutic" and the like indicates any molecule that has a significant effect on the body to treat or prevent conditions or diseases.

"Pharmaceutically active agent" means any of a drug, therapeutic agent, pro-drug or diagnostic.

"Hydrophobic Drug" means any pharmaceutically active agent that is only soluble in water at less than 50 mg/L at 25° C.

"Anti-proliferative agent" means a molecule that acts to inhibit proliferative events. Examples of anti-proliferative agents include but are not limited to paclitaxel, carboplatin, cisplatin.

Discussion of Exemplary Diseases

The delivery system may be advantageous as a treatment strategy for various cancers.

Cancers:

The system is also particularly useful for treatment of cancers including prostate, breast, ovarian, bladder, brain, liver, gastric, head and neck.

Prostate Cancer

Prostate cancer is the most common male malignancy in the Western world. In the United States, approximately 190,000 patients will be diagnosed with prostate cancer each year. During the same time period, 40,000 men will die from this disease. The cancer may remain locally within the prostate, but it tends to spread to surrounding tissues or to distant sites such as the lymph nodes and bone during more advanced stages of the disease.

Current treatment therapies for individuals diagnosed with prostate cancer depends on the stage of the disease, and the patient's age and health. Prostate cancer is commonly treated using radiation therapy, hormone withdrawal or castration (surgical or chemical), anti-proliferative agents, and surgery. Treatment for prostate cancer that has metastasized involves the removal of the testicles or hormone therapy. Both are used to minimize or inhibit the production of the testosterone that is aiding cancer growth. Approximately 20% of all prostate cancer patients undergo hormone withdrawal therapy. Hormone therapies include goserelin acetate (Zoladex.RTM.) or leuprolide acetate (Lupron.RTM.). Anti-proliferative agents such as 5-fluorouracil and paclitaxol are also used to treat prostate cancer. The polymeric implant system is advantageous for early stage disease because it can provide sustained release of drugs or hormones directly at the tumor site. An implant, gel, film or paste of PoLi containing hormone therapy or anti-proliferative agents, alone or in combination, would be placed at the site of tumor resection, or injected into the tumor to achieve the anti-tumor effect.

Brain Cancer

Approximately 19,000 individuals are diagnosed with primary intracranial (brain) cancer each year in the U.S. Patients with these tumors often result in neural psychological disorders such as motor dysfunction, seizures, and vision abnormalities. The most commonly developed brain tumors are gliomas, astrocytomas, brain stem gliomas, ependymomas and oligodendrogliomas. Treatment of brain tumors may involve surgical removal of the tumor, radiation therapy and chemotherapy. Antiproliferative agents such as cisplatin are commonly administered in conjunction with surgery and radiation therapy. It is also used to combat against recurrent tumors. Polymeric implants containing cisplatin can be placed within the tumor resection site to minimize or prevent recurrent tumors by providing a long-term sustained release of the drug at the site of tumor development.

Breast Cancer

Breast Cancer is one of the most common malignancies in women with approximately 200,000 new cases diagnosed each year in the U.S. This accounts for 30% of all cancers diagnosed in women. The incidence of breast cancer has continued to rise over the past two years, which is partially associated with increased screening by self-exam and mammography. (Vogel V G: Cancer J Clin (2000) 50(3): 156-70).

There are several drugs on the market aimed at treating different types of breast cancer. These drugs can be classified into six groups; Estrogen Antagonists, Aromatase Inhibitors, Cyclophosphamides, Anthracyclines, Taxols, and Anti-metobolites (5-Fu). More recently, monoclonal antibody treatments for breast cancer have been brought onto the market. These are used to effectively treat a subset of patients that express HER2 receptors on the surface of their cancer cells.

Two important determinants of the treatment options are the type of tumour and the stage of progression. Prognostic factors, such as tumour size, expression of estrogen and progesterone receptors, cell cycle phase, her-2-neu protein expression, and tumour ploidy, will play a role in determining the optimal treatment regimen. (Winchester D P et al. CA Cancer J Clin (2000) 50(3): 184-200).

Hormone responsive Stage I or Stage II breast cancer would be treated with a combination of tamoxifen and aromatase inhibitors within PoLi implants, film, gel or paste formulations placed intratumorally or within the area of tumor resection.

Significant lymph node involvement, characteristic of Stage III or Stage IV breast cancer may require mastectomy and removal of auxiliary lymph node. Treatment of metastatic disease usually involves radiation therapy and chemotherapy, including anthrocyclines, cyclophosphamides, taxanes and HER2 antagonists. Anti-proliferative agents such as 5-Fluorouracil, Doxorubicin, Methotrexate and Paclitaxel are currently used as chemotherapy for breast cancer and are administered orally or intravenously. Stage III or Stage IV breast cancer can be treated by local administration (breast and lymph nodes) of these drugs alone or in combination, within PoLi implants, film, gel or paste formulations placed intratumorally or placed within the area of tumor resection.

Gastric Cancer

Gastric Cancer is ranked 14th in incidences among major types of cancer malignancies in the US. In 1998, approximately 24,000 new cases of gastric cancer are diagnosed each year in the US and there are about 700,000 new cases diagnosed worldwide. Alarmingly the average age of onset has been falling in the past two decades. Survival varies from months to years depending on the cancer stage and the response to therapy. Gastrectomy is the most common form of treatment and local adjuvant therapy will be beneficial to reduce the chances of re-operation. 5-fluorouracil, cisplatin, doxorubicin, etoposide, mitomycin, 6S-leucovorin and filgrastim are commonly used chemotherapeutic agents against gastric cancer. Cascinu S. et al. J Clin Oncol (1997) 15: 3313-3319). The utilization of the Poli, formulated as an implant, film, gel or paste containing anti-proliferative agents, when placed inside, the colon, provides continuous release within the lower intestinal tract for treatment of gastric cancer.

Liver Metastases

Metastatic or subsidiary liver tumors spread to the liver from a cancer elsewhere in the body. The liver's main functions is to filter blood, therefore cancer cells from other parts of the body become lodged in the liver and become tumors. The most common type of metastatic liver tumors are those caused by colon cancer that has spread to the liver. Also, the incidence is common in hormone producing tumors, gastrinoma, insulinoma and carcinoid. Approximately 50% to 60% of patients with colorectal cancer will develop hepatic metastases during the course of their illness. In nearly a quarter of these patients the liver is the only site of disease. (Sasson A R et al. Semin Oncol. (2002) 29(2): 107-18). A curative mode of treatment can only be taken in the early stages where chemotherapy is used as neoadjuvant or adjuvant therapy. Common agents are leucovorin, adriamycin, VP-16, cisplatin and 5 FU. [1]. Poli solution, slurry, implant, film, gel or paste would be administered intraperitoneally for optimal effect on liver cancers.

Ovarian Cancer

Ovarian cancer is a disease produced by the rapid growth and division of cells within one or both ovaries. About 1 in every 57 women in the United States will develop ovarian cancer (NIH Publication No. 00-1561) and it remains the 5th leading cause of cancer death amongst women (American Cancer Society Statistics 2002).

Treatment of ovarian cancer depends on a number of factors, including the stage of the disease and the general health of the patient. Surgery is the initial treatment for women diagnosed with ovarian cancer. After surgery, chemotherapy may be given to destroy any cancerous cells that may remain in the body in order to control tumor growth. At this time the standard of care for postoperative chemotherapy includes cycles of paclitaxel (PTX) and carboplatin (CPT). Unfortunately, treatment with these agents is accompanied by "cumulative and/or irreversible toxicities" which is mostly attributed to systemic drug exposure (Dunton C. J., Oncologist (2002), 7 (suppl 5): 11-19). In addition, while these tumors are initially responsive to chemotherapy most patients relapse eventually with drug resistant disease. In recent years, many clinical trials have demonstrated that intraperitoneal (IP) administration of chemotherapy provides benefits in terms of both increasing efficacy and decreasing systemic toxicity. Intraperitoneal delivery and controlled release of both PTX and CPT using PoLi implants, film, gel, slurry solution, or paste, have been shown to be equally efficacious and less toxic than formulations that do not take advantage of controlled release mechanisms.

Head and Neck Cancer

Head and neck cancers are often referred to as squamous cell carcinomas as these cancers begin in the squamous cells that line the structures found in the head and neck. Cancers of the head and neck are further identified by the area in which they begin: Oral cavity, Salivary glands, Paranasal sinuses and nasal cavity, Pharynx (Nasopharynx, Oropharynx, Hypopharynx), Larynx and Lymph nodes. Head and neck cancers account for 3% of all cancers in the United States. It is estimated that almost 38,000 men and women in the United States will develop head and neck cancers in 2002 [NCI].

Current therapy for head and neck cancers include surgery, radiation, and chemotherapy, either alone or in combination. Combined modality therapy is becoming the principal method of treating patients with locally advanced head and neck cancers. Currently, researchers are investigating new treatments such as gene therapy. Chemotherapeutic agents, such as Taxol, Taxotere, Gemzar and Doxil are being combined with established chemotherapeutic agents to improve results. For head and neck cancers affecting the Paranasal sinuses or nasal cavity, nasal spray, gel, slurry, or paste formulations of PoLi which contain appropriate anti-proliferative agents are the most effective. For cancers affecting salivary glands and the oral cavity, an intratumoral placement of PoLi with appropriate anti-proliferative agents would be preferable.

Bladder Cancer

Bladder cancer accounts for approximately 90% of the cancers of the urinary tract including the renal pelvis, ureters, bladder and urethra. The National Cancer Institute (NCI) states that bladder cancer is diagnosed in 38,000 men and 15,000 women every year in the United States alone. This is the fourth most common type of cancer in men and the eighth most common type in women. It is three times more likely to occur in men than women. The incidence of bladder cancer increases with age dramatically. People over the age of 70 develop the disease 2 to 3 times more often than those aged 55-69 and 15 to 20 times more often than those aged 30-54.

Treatment for bladder cancer depends on the type of cancer, the stage of the disease and the patient's age and overall health. Treatment options include: surgery, chemotherapy, radiation, and immunotherapy. Treatments may be combined (e.g. surgery or radiation and chemotherapy). In advanced stages of the disease, partial or radical removal of the bladder (cystectomy) is performed. Radiation therapy may be used after surgery to destroy any remaining cancer cells. Immunotherapy is used to enhance the immune system to destroy cancer cells by using BCG (a vaccine derived from the bacteria that causes tuberculosis) that is infused through the urethra into the bladder, once a week for 6 weeks. Alternatively, the PoLi implant, film, gel, slurry, solution or paste containing BCG would be administered locally at the time of surgery to provide controlled release of the active compound.

Chemotherapeutic agents used in the treatment of bladder cancer include: 5-fluorouracil, cisplatin, methotrexate, valrubicin (Valstar™), thiotepa (Thioplex®), mitomycin, and doxorubicin (Rubex®). These drugs are administered orally or intravenously before and/or after surgery. In early bladder cancer, intravesical chemotherapy (infused into the bladder through the urethra) may be recommended. Liquid or gel formulations of PoLi containing anti-proliferative agents would be injected intravesically to allow for controlled release of compounds in the bladder. Alternatively, solid formulations such as an implant or film could be surgically inserted into the bladder.

DETAILED DESCRIPTION

Polymer-lipid or PoLi, is a unique formulation that provides controlled release of hydrophilic agents, hydrophobic agents or combinations of hydrophilic and hydrophobic agents. The system consists of a polymer-lipid matrix that is formed from a chitosan based material and phospholipid mixed in specific proportions. Chitosan (CHi) is a naturally occurring biodegradable, biocompatible polysaccharide that has been investigated for use in a variety of biomedical applications including wound dressings, sutures, artificial skin, tissue engineering and drug delivery. CHi is the deacetylated form of chitin and consists of 1→4 linked 2-amino-2-deoxy-β-D-glucopyranose. Preferably the chitosan based material comprises 85% chitosan and 15% chitin. The degradation of CHi produces glucosamine and N-acetylglucosamine residues. Glucosamine is an amino sugar that is naturally produced in the body. CHi-based implants have been shown to last months in vivo with negligible foreign body reaction. In addition, these systems do not evoke a chronic inflammatory response and significant fibrous encapsulation does not occur. In the past, CHi-based films and gels have been commonly prepared by chemical crosslinking with agents such as glutaraldehyde. In more recent years various groups have exploited non-covalent crosslinking as a means to produce CHi hydrogels. These hydrogels are suited for use as biomedical implants owing to their complete biodegradability. In the current system the phospholipid molecules are used in combination with CHi to achieve a physically crosslinked system.

Various phospholipids have been studied as possible components for this formulation and discovered that the nature of the lipid headgroup (i.e. PC versus PE versus PG) as well as the amount of lipid employed controls the physico-chemical properties of the system. By carefully choosing the appropriate lipid component either films for implantation or solutions which gel in-situ following injection can be prepared. Preferably the Chi to phopholipid ratio is from about 0.03:1 to 2.5:1.

The pharmaceutically active agents may be formulated by dispersion or dissolution within the polymer-lipid matrix. However, in some cases they may also be formulated by incorporation into particles, such as nanoparticles, liposomes and hydrophilic polymers, that are in turn dispersed within the matrix. In this case, the particles act as "cargo space" for the drugs while the polymer-lipid matrix provides a shield or barrier to ensure controlled release. The particles may be formed from polymer or lipid or a mixture thereof. Specifically the pharmaceutically active agent may be either hydrophilic or hydrophobic. The drug delivery composition may also include more than one pharmaceutically active agent.

For example, a hydrophobic drug, such as Taxol, has been formulated by incorporation into poly (d,l-lactide) nanoparticles which are then dispersed throughout the film. A hydrophilic drug, such as Carboplatin, may be formulated by dissolution within the matrix or incorporation into liposomes.

Preferably the method of manufacturing the drug delivery system is achieved by dissolving a chitosan based material in a solution of distilled water and acetic acid. Preferably the chitosan based material is combination of 85% chitosan and 15% chitin. Preferably a phopholipid is dissolved in ethanol and the solutions mixed at a temperature above the phase transition of the phospholipid. The phospholipid may be, by way of example only, phosphatidylcholine, egg phosphatidylcholine, phosphatidylglycerol, phosphatidylethanolamine. The resulting phospholipid to chitosan ratio preferably may range from 0.03:1 to 2.5:1 w/w. The final mixture is blended to form a homogenous mixture for 15 minutes and then placed in a PFA teflon coated petri dish and dried in a dessicator containing silica for 5 days at room temperature thereby forming a cross-linked matrix for the control release of a pharmaceutically active agent.

The incorporation of at least one pharmaceutically active agent may be incorporated into the drug delivery system in two different methods. The first method preferably includes the preparation of nanoparticles via an emulsification-diffusion method by dissolving poly(d,l-lactide)-b-poly(ethylene oxide) (PLA-b-PEO) copolymer, PLA homopolymer and the pharamaceutically active agent, paclitaxel (PTX) in ethyl acetate. The mixture is preferably diluted with distilled water and mixed and diluted with water again. Preferably the solution is dialyzed to remove the organic solvent and lyophilized to obtain a dry powder.

Preferably the dry powder is re-suspended in distilled water and then added to the chitosan-ePC (1:0.8 w/w) solution described above. This resulting solution is preferably vortexed, homogenized and then placed in a dessicator for 5 days at room temperature to form the resulting implant shown in FIG. 1.

Preferably the second method of incorporating a pharmaceutically active agent into the drug delivery composition includes dissolving a high concentration of Carboplation was first dissolved in distilled water. The resulting Carboplation solution may then be used to dissolve 2% (w/w) chitosan (set out above) with further mixing. Preferably the chitosan-carboplatin solution is mixed and homogenized with egg phosphatidylcholine, dissolved in warmed ethanol. Preferably the final carnoplatin-chitosan-lipid solution is dried in a dessicator for 5 days at room temperature. Preferably the drug:matrix ratio of for either method is 1:7 as illustrated in Example 12 below.

As outlined above there are various cancers in which the current invention would be utilized. The drug delivery composition outlined above affords two different methods of delivering in a controlled release fashion at least one pharmaceutically active agent. Depending on the cancer being addressed, preferably the appropriate pharmaceutical agent may be included in the resulting cross-linked chitosan and phospholipid matrix. Preferably the pharmaceutically active agent may either be encapsulated or mixed directly into the matrix. As further described in the examples set out below, the encapsulation of paclitaxel in nanoparticles that are embedded in the drug delivery system has significant impact on ovarian cancer tumour growth in CD-1 mice.

Furthermore as described in more detail in the examples outlined below (examples 14 and 17), the strong linear correlation ($R2=0.975$) between the disclosed release rate data for the in vivo and in vitro examples indicates that the in vitro model of the drug delivery composition is a good representation of the drug delivery composition in vivo. Specifically a comparison was made between PTX-chitosan-ePC implants values in vitro and those obtained from the in vivo studies for the release of nanoparticle encapsulated PTX from the PTX-chitosan-ePC implant. The results indicate consistency between the in vitro and in vivo release rates thereby providing a significant benefit over known drug delivery compositions. Specifically the correlation allows for the utilization of the in vitro model to be a clear indicator of release rates of other pharmaceutically active agents for the in vivo model. This indicator therefore supports a wider application of the drug delivery composition to pharmaceutically active agents which in turn treat various forms of cancers.

The present invention will be further understood by reference to the following non-limiting examples:

EXAMPLES

Example 1

Demonstration of Process to Prepare Implantable Polymer-Lipid Films

The initial step (Step (1)) is to dissolve chitosan (85% chitosan, 15% chitin) in 20 ml of distilled water containing 1% (v/v) acetic acid. In the next step (Step (2)) lipid (phosphatidylcholine, phosphatidylglycerol, phosphatidylethanolamine) is dissolved in warmed ethanol (at temperature above phase transition of lipid components). The chitosan and lipid solutions are then mixed (Step (3)) such that the lipid to CHi ratios range from 0.03:1 to 2.5:1 w/w. The mixture is then blended (Step (4)) by vortexing for 3 minutes and then homogenizing (Polytron® PT-MR 3100, Kinematica AG) at 2000 rpm for 15 minutes. The chitosan-lipid solution is then placed in a PFA teflon coated petri dish (Chemware Laboratory Products) and dried (Step (5)) in a dessicator containing silica for 5 days at room temperature.

Example 2

Demonstration of Effect of Composition on Film Properties, Swelling and pH

A 10 mm×10 mm dry chitosan-lipid film was placed in 10 ml of buffer (0.01 M PBS) and incubated at 37° C. The film was removed from the vial after selected time periods, blotted dry and weighed prior to being placed into a new vial containing fresh buffer. The pH of each buffer was measured prior to adding the film and following the removal of each film. After 24 hours, the film was dried and the swelling ratio (Q) was calculated using the following equation: $Q=(Wf-Wd)/Wd$; where Wf is the weight of the film after each time point and Wd is the weight of the final dry film. The maximum swelling ratio (QM) is defined as the highest value of Q attained over the 24 hours of analysis. The percent weight loss (WL) of each film following the 24 hour incubation period in buffer was calculated using the equation: $WL=[(Wi-Wd)/Wi]\times100$; where Wi is the initial weight of the film and Wd is as above.

The swelling profile, during 24 hours of incubation in PBS, was measured for films prepared from chitosan and phospholipid mixed in varying proportions. The 1% and 2% chitosan films with no phospholipid swelled extensively when placed in buffer at 37° C. These films fell apart following the first hour of incubation and were almost completely dissolved within 24 hours. Therefore, in order to produce stable films, phospholipid was added in an attempt to achieve physical crosslinks between the chitosan chains. Indeed, the swelling studies revealed that the addition of lipid to the film did enhance stability when compared to films prepared from chitosan alone. As summarized in Table 1 of FIG. 11, the maximum swelling ratios (Qm) for the chitosan-lipid films were found to range from 1.3 to 43.8 depending on the nature and amount of lipid present within the film. The nature of the lipid head group (PC vs. PE vs. PG) had a pronounced impact on the swelling of the film. As shown in Table 1 of FIG. 11, Q varied from 17.1 to 43.8 when the lipid was changed from DMPC to DMPG and when DMPE was the lipid employed the film was too fragile for Q to be measured.

The relative hydrophobic nature of the choline headgroup may contribute to its stronger interaction with chitosan, in comparison to the PG and PE headgroups. Since DMPC, the lipid with the choline headgroup, appeared to be most favourable we explored DPPC and ePC as the lipid component. Interestingly, the use of DPPC resulted in an unstable film that began to swell and degrade rapidly in buffer (i.e. Q could not be measured). By contrast, the addition of ePC to chitosan afforded films with low values for Q that ranged from 5.9 to 1.3 as the amount of lipid was increased (Table 1). These swelling studies reveal that ePC is most suitable as the phospholipids component of the film. The lipid-chitosan film is likely stabilized by a combination of ionic, hydrogen bonding and hydrophobic interactions. Hydrogen bonding and ionic interactions are expected to contribute more to the film's stability than hydrophobic interactions. This is confirmed by the fact that DPPC(C-16 hydrocarbon tail) was unable to produce stable films, however, DMPC(C-14 hydrocarbon tail in combination with chitosan resulted in a stable film with $Q_m=17.1\pm0.9$.

Figure 2:
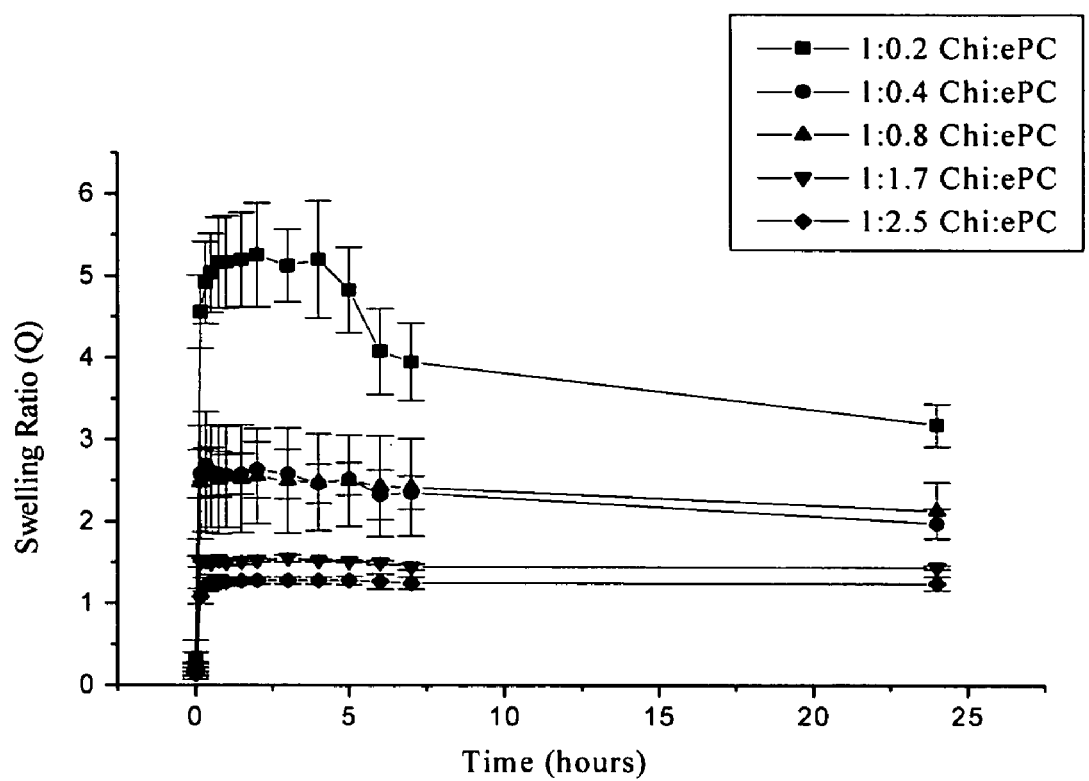
FIG. 2. Swelling profiles of the PoLi implant system containing different ratios of chitosan: pure egg PC (1:0.2, 1:0.4, 1:0.8, 1:1.7, 1:2.5) over 24 hours.

The swelling behaviour of films prepared from chitosan and crude or pure ePC was similar despite the difference in their composition (Table 1 of FIG. 11). Pure ePC consists of a mixture of unsaturated and saturated PC lipids with hydrocarbon chains of varying lengths (i.e. C16-C20). Crude ePC consists of at least 60% PC while the remaining 40% is mostly PE and other phospholipids. In FIG. 2, we present the swelling profiles for films prepared from pure ePC and chitosan. As shown, the maximum swelling ratio for each film was reached within 1-2 hours of incubation and the ratio leveled off at a constant value following 6 hours. Interestingly, although the overall degree of swelling of the films decreased with an increase in lipid content it appeared that this relationship (i.e. degree of swelling and lipid content) was not linear.

Figure 3:
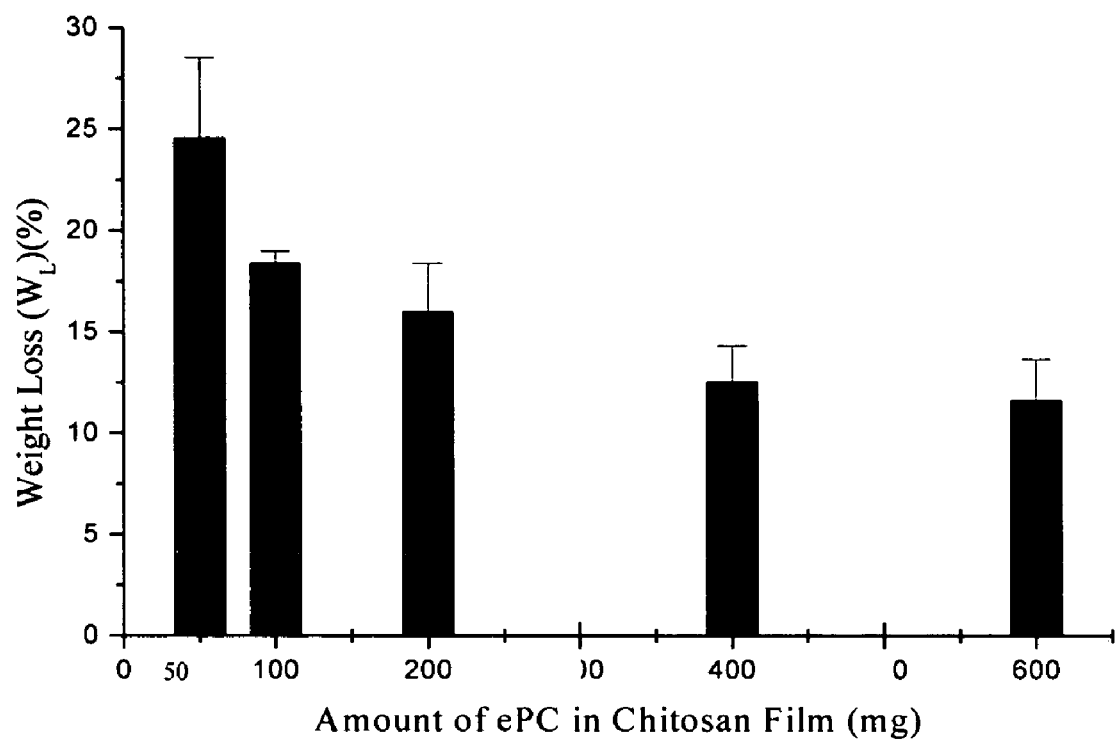
FIG. 3. The percent weight loss (WL) of each film following the 24 hour incubation period in buffer. WL=[(Wi−Wd)/Wi]×100; where Wi is the initial weight of the film and Wd as above (chitosan: pure egg PC (1:0.2, 1:0.4, 1:0.8, 1:1.7, 1:2.5) are equivalent to 50 mg, 100 mg, 200 mg, 400 mg, 600 mg ePC, respectively).

Specifically, it was found that the degree of swelling of films prepared from chitosan to lipid ratios of 1:0.4 and 1:0.8 were approximately equal. Likewise the degree of swelling was comparable for films consisting of chitosan to lipid ratios of 1:1.7 and 1:2.5 (w:w). Similarly, this trend was also observed in the values obtained for the percent mass lost for each film over the 24 hour swelling period. As shown in FIG. 3, the films prepared from the chitosan to lipid ratios 1:0.4 and 1:0.8 had WL values of 18.4%±3.9 and 16.0%±2.4, whereas the films containing 1:1.7 and 1:2.5 chitosan to ePC had values of 12.6%±1.7 and 11.6%±2.0. Therefore, increasing the lipid content within the film results in a non-linear decrease in swelling and non-linear increase in the stability of the implant. It should be noted that a film could not be formed from lipid alone; use of lipid alone resulted in a gel with no structural integrity.

The pH profiles of the chitosan-ePC films were monitored over a 24 hour period. Incubation of films prepared from chitosan alone in PBS caused an initial decrease in the pH of the buffer from 7.4 to 6.8. By contrast, the films prepared from chitosan and ePC did not cause a marked decrease in the pH of the buffer. In these solutions, the pH ranged from 7.2-7.4 over the entire 24 hour period. The decrease in pH of the buffer results from the release of acetic acid from the film. It is hypothesized that the lipid molecules interact with chitosan resulting in the displacement of acetic acid which may then evaporate during film preparation. Therefore, films formed from chitosan and lipid contain less acetic acid and cause only a marginal decrease in the pH of the buffer in comparison to films prepared from chitosan alone.

Example 3

Demonstration of Incorporation of Paclitaxel, a Hydrophobic Drug, into PoLi Implant Nanoparticles were prepared via an emulsification-diffusion method. Briefly, 32 mg poly(d,l-lactide)-b-poly(ethylene oxide) (PLA-b-PEO) copolymer, 80 mg PLA homopolymer and 32 mg paclitaxel (PTX) were dissolved in 5 ml ethyl acetate. 5 μCi of 3H-PTX was added to the PTX solution. The ethyl acetate mixture was then added to 10 ml of distilled water. The solution was mixed (vortexed, homogenized or sonicated) for 5 minutes and diluted with 8 ml of water. The solution was then placed in dialysis membrane (spectrum laboratories Inc.) (MWCO: 8000) and dialyzed against 2 liters of water to remove the organic solvent. Following dialysis, the nanoparticles were lyophilized (FreeZone® 6 Liter Freeze Dry System, Labconco Corp., Kansas City, Mo.) to obtain a dry powder.

The dry powder, consisting of PLA-PEG nanoparticles loaded with 3H-PTX, was resuspended in 3 ml of distilled water and added to 12 ml of the chitosan-ePC (1:0.8 w/w) solution. This solution was vortexed for 3 minutes and homogenized at 2000 rpm for 15 minutes and then placed in a dessicator containing silica for 5 days at room temperature. A schematic of the PoLi hybrid implant system is shown in FIG. 1.

Example 4

Demonstration of In-Vitro Release of Paclitaxel from PoLi Implant

The release kinetics of the 3H-PTX-loaded PoLi implant system was evaluated over a two-month period. The drug-loaded implant was incubated in phosphate buffer saline (PBS) (0.01M, pH=7.4) containing either 2 mg/ml lysozyme or 2 mg/ml lysozyme and 5 mg/ml bovine albumin at 37° C. At given time intervals, 2.5 ml of solution was withdrawn from each vial for analysis and replaced with 2.5 ml of fresh media. The concentration of PTX in the withdrawn solution was analyzed by scintillation counting. From the scintillation results, we plotted the percent cumulative release of 3H-PTX from the PoLi implant system over a two-month period.

Figure 4:
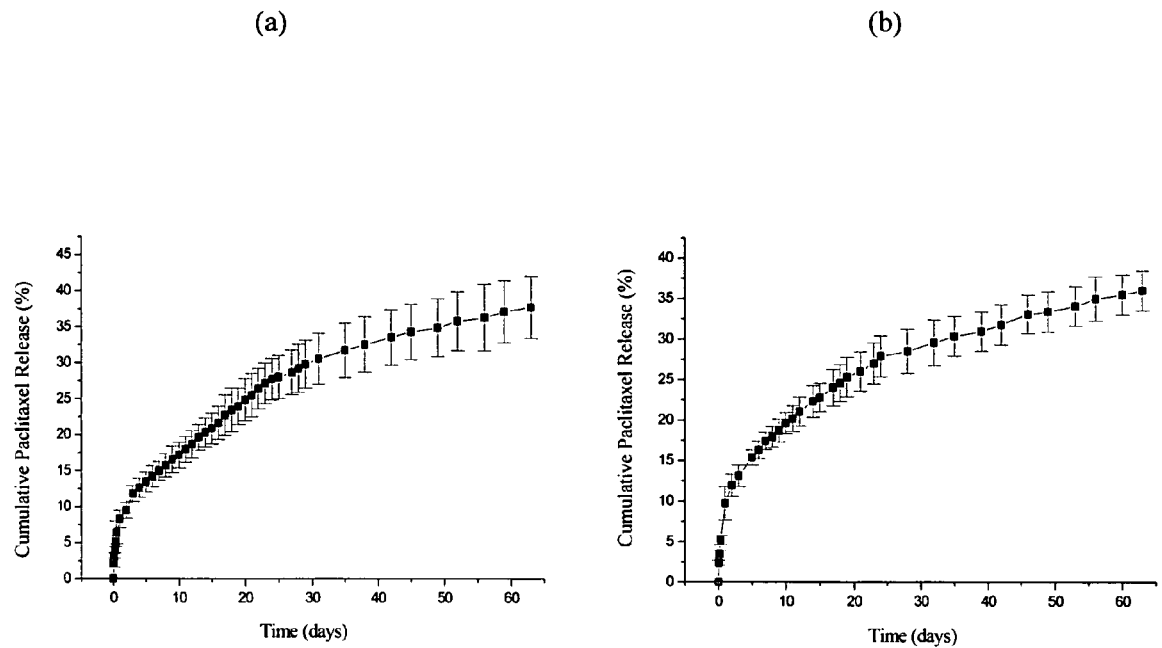
FIG. 4. Percent cumulative release of tritium labelled paclitaxel from the PoLi implant system incubated in (a) PBS buffer (pH=7.4) containing 2 mg/mL lysozyme or (b) PBS buffer (pH=7.4) containing 2 mg/mL lysozyme and 5 mg/mL bovine albumin at 37° C. over a 63 day period (n=3).

A first order release profile was observed for PTX from the PoLi implant in PBS containing lysozyme and PBS containing lysozyme and albumin. The PoLi implant was placed in a lysozyme-containing solution for the release studies since chitosan is primarily degraded by lysozyme in vivo. In addition, albumin was also added to the release media for physiological relevance. During the incubation in the lysozyme solution, a release rate of 0.4% of total drug loaded per hour was observed during the first 3-9 hours of the study. This drug release rate may be attributed to the loosely attached nanoparticles on the surface of the film. A rate of 0.8%/day and 0.3%/day was obtained over days 4-30 and 31-63 respectively. (FIG. 4a). These in-vitro studies were performed on a film prepared from a CHi: ePC ratio of 1:0.8. From our swelling studies, we may infer that the rate of drug release may be altered by changing the lipid content within the film. Similar release rates were obtained for the film when incubated in buffer containing lysozyme and albumin (0.6%/hr (3-9 hrs), 0.8%/day (days 4-30) and 0.2%/day (31-60 days) (FIG. 4b). Therefore, the addition of albumin did not cause any further increase in PTX release. Following 63 days of incubation, a total of 36-38% of the drug loaded was released from the PoLi implant system which originally contained approximately 80 μg of PTX. Changing the weight or size of the implant can also modify the total amount of drug released.

First order kinetics is typical for a reservoir type polymer lattice. Petraos et al. described the ideal hydrogel for drug delivery as a matrix loaded with drug that would provide a zero or first order release profile without changing the geometry of the implant or diluting the drug. From the results above, diffusion of PTX as well as swelling and physical erosion of the implant contributes to the overall release of the drug. The system has been shown to provide slow and controlled release of PTX with a minimal burst release of only 10% (approximately 8 μg) within the first 24 hours and a sustained release in-vitro over the entire two-month period.

Example 5

Demonstration of Incorporation of Carboplatin, a Hydrophilic Drug, into PoLi Implant A high (120 mg) concentration of Carboplation was first dissolved by heating and stirring in purified distilled water. Secondly, a 2% (w/w) chitosan solution was prepared as described above with the exception of using the carboplatin solution to dissolve the chitosan. The chitosan-carboplatin solution was then vortexed and left overnight. 200 mg of egg phosphatidylcholine, dissolved in warmed ethanol, was blended with the chitosan solution, vortexed for 3 minutes and then homogenized at 2000 rpm for 15 minutes. The carnoplatin-chitosan-lipid solution was then placed in a PFA teflon coated petri dish (Chemware Laboratory Products) and dried in a dessicator containing silica for 5 days at room temperature.

Example 6

Demonstration of Incorporation of Carboplatin into PoLi Implant using Liposomes Multilamellar liposomes were prepared using the thin-film hydration method. Mixture of 90 mol % ePC and 10 mol % cholesterol were dissolved in chloroform at 60° C. The solution was dried down with nitrogen and a thin film was formed. The solvent was removed by placing the film overnight in a vacuum at 30 in. Hg at room temperature. The lipid film was then hydrated at 60° C. with 14 mg/ml carboplation in HBS (HePes) buffer (pH 7.4) at a lipid concentration of approximately 200 mg/mL. These multilamellar liposomes were then sized down to form unilamillar liposomes through high-pressure extrusion (10 mL Lipex™ Extruder, Northern Lipids Inc., Vancouver, British Columbia, Canada). To obtain liposomes of approx. 100 nm in diameter, a polycarbonate membrane (Nucleopore® Track-Etch Membrane, Whatman, Northern Lipids Inc., Vancouver, British Columbia, Canada) with pore size of 80 nm were used for 10 extrusions. The liposomes were dialyzed against distilled water for 2 hours. A 6 ml liposome solution was added to 10 ml of 2% chitosan solution (prepared as above), mixed and dried.

Example 7

Demonstration of In-Vitro Release of Carboplatin from PoLi Implant

The release kinetics of the free carboplatin-loaded and carboplatin loaded liposomes within PoLi implant system were evaluated over a one-month period. The implants were incubated in phosphate buffer saline (PBS) (0.01M, pH=7.4) containing 2 mg/ml lysozyme at 37° C. At given time intervals, 4 ml of solution was withdrawn from each vial for analysis and replaced with 4 ml of fresh media. The concentration of carboplatin in the withdrawn solution was analyzed by ICP. From the results, the percent cumulative release of carboplatin from the PoLi implant system over a one-month period was plotted.

Figure 5:
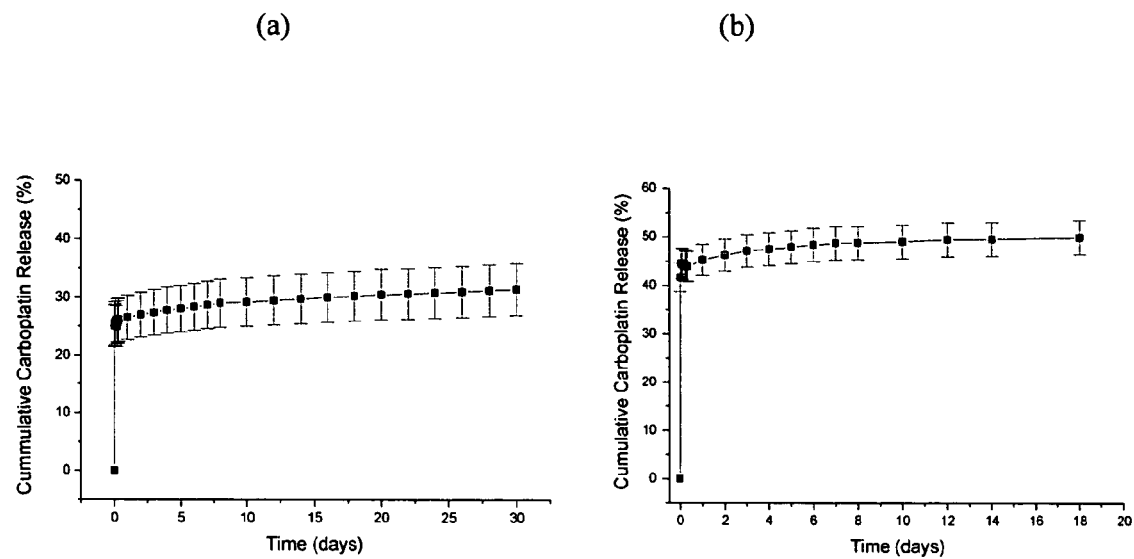
FIG. 5. Percent cumulative release of free carboplatin (a) and carboplatin encapsulated within liposomes (b) from the PoLi implant system incubated in PBS buffer (pH=7.4) containing 2 mg/mL lysozyme at 37° C. over a 30 day period (n=3).

A total of 72 mg of free carboplatin was loaded within the PoLi implant system. A burst release of 29% carboplatin from the implant was observed during the first hour of incubation. A sustained release of 0.2%/day was obtained over days 1 through 30 (FIG. 5A).

Preliminary results from the liposomes containing carboplatin showed a burst release of 42% from the PoLi implant system during the first hour of incubation. A sustained release of 0.3%/day was obtained over days 1 through 18 (FIG. 5B).

Example 8

Prolonged Exposure to Chemotherapeutic Agents Increases Efficacy

Tumour sensitivity to CPT and PTX was determined by IC50 cell viability using the MTT assay as described below.
Cell Proliferation Assays (MTT Method)

The IC50 (drug concentration causing 50% inhibition of clonogenic survival) of PTX and CPT was determined on each cell line using the 3-(4,5-dimethylthiazol-2-yl)-2,5-diphenyltetrazolium bromide (MTT) assay. Briefly, cells were diluted with culture medium to the seeding density (105 cells/mL) and suspended in 96-well tissue culture plates (100 μL/well), and preincubated at 37° C. overnight. Cells were then treated continuously with 10 μL of various concentrations of the anticancer agents to obtain a dose-response curve for each agent. For combination assays, cells were also treated continuously with a total of with 10 μL of various concentrations of PTX and CPT. Each drug concentration was as follows: 6.25-200 ng/mL PTX and 1-50 μg/mL CPT.

After incubation of 24, 48 and 72 h, 10 μL of MTT solution (5 mg/mL of PBS, filtered) was added to each well and the plates were further incubated for 4 h. 100 μL of extraction buffer (20% w/v SDS dissolved at 37° C. in a solution of 50% Dimethylformamide/50% H2O, 2.5% of 80% Acetic acid 2.5% of 1N HCl (ph 4.7)) was added to solubilize the MTT-formazan product. Absorbance at 570 nm was measured with a microplate reader (SPECTRAmax® PLUS384, Molecular Devices, Sunnyvale Calif.—U.S.A.). Dose response curves were plotted as a percentage of the control cell number, which was obtained from the no-drug exposure sample. A semilog scale was used when necessary: IC50 of CPT for SKOV3 and CAOV3.

Figure 6A:
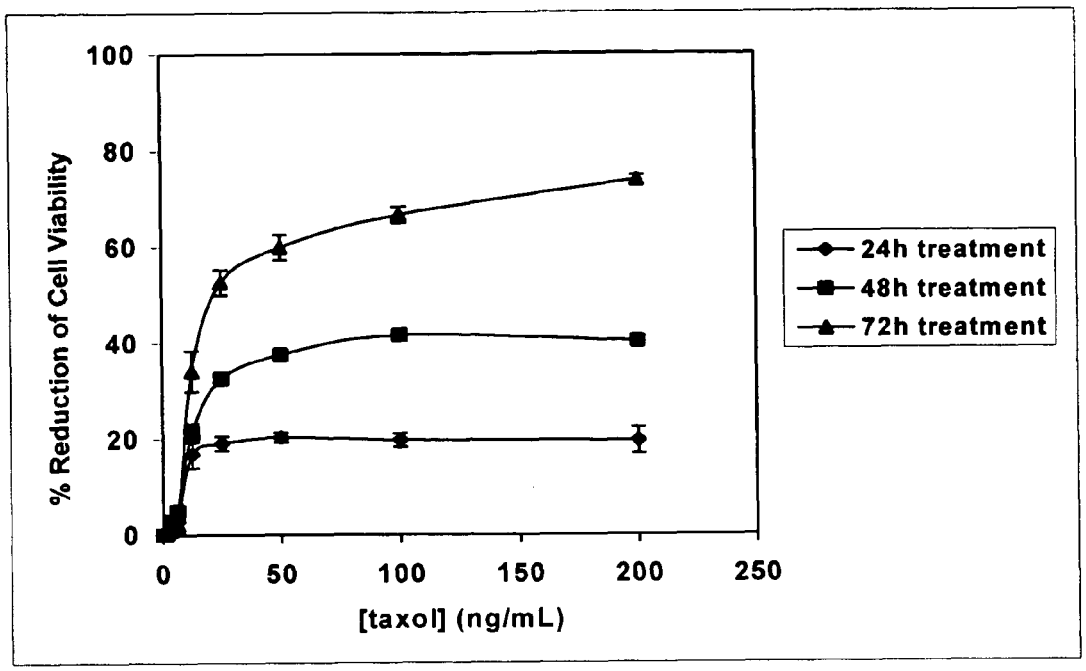
FIG. 6A. Enhanced chemosensitivity of SKOV3 ovarian cancer cells to sustained exposure to PTX.

The concentration of CPT required to reduce the cells proliferation by 50% decreases with time. All the IC50 values for SKOV3 and CAOV3 cells at the different time points are presented in table 2 of FIG. 12. A 10 fold decrease in PTX concentration was observed for the IC50 of the SKOV3 cells when comparing the 24 and 72 hour time point (FIG. 6). Similar values were shown for CAOV3 cells treated with PTX and CPT. A decrease in IC50 was also observed for the SKOV3 cells treated with CPT, however it was not as drastic as the SKOV3 cells treated with PTX or the CAOV3 cells treated with PTX FIG. 12.

Example 9

Combination of CPT and PTX Increases Efficacy

The effect of combining PTX and CPT increased the percent cell viability when compared to each drug alone (FIGS. 7A, 7B). The PTX IC50 was greater than 200 ng/ml however, when CPT was added (10 ng/ml) a >20 fold increase in chemosensitivity occurred. Similarly, the CPT IC50 was 35 μg/ml and when PTX was added (10 μg/ml) a 3.5 fold increase in chemosensitivity was observed.

Example 10

Demonstration of Biological Activity of Paclitaxel and Carboplatin Released from PoLi Implant in-Vitro (Cell-Culture)

In-vitro cytotoxicity of the implant, implant containing PTX and free PTX. The SKOV-3 cells were plated in 6-well plates and cultured in RPMI 1640 supplemented with 1% penicillin/ streptomycin solution and 10% fetal bovine serum. The cell line was grown at 37° C. in a humidified incubator equilibrated with 5% CO2. Medium was replaced three times a week and cells were typsinised and subcultured every five days. Aliquots of a PTX stock solution dissolved in ethyl acetate were added to wells such that the final concentration of PTX ranged from 5 to 22 μg. Likewise, PoLi implants of varying sizes were added to the wells. The implants were swelled in 70% ethanol for sterilization purposes prior to incubation with cells. Following a 48 hour incubation period the cell viability was measured using the MTT assay. The MTT dye was added to each well following the specific time period and incubated for 2 hours at 37° C. Cells were then solubilized in 10% SDS. Formazan dye concentrations were then detected using a microplate reader (BioRad) at emission wavelength of 570 nm.

Figure 6B:
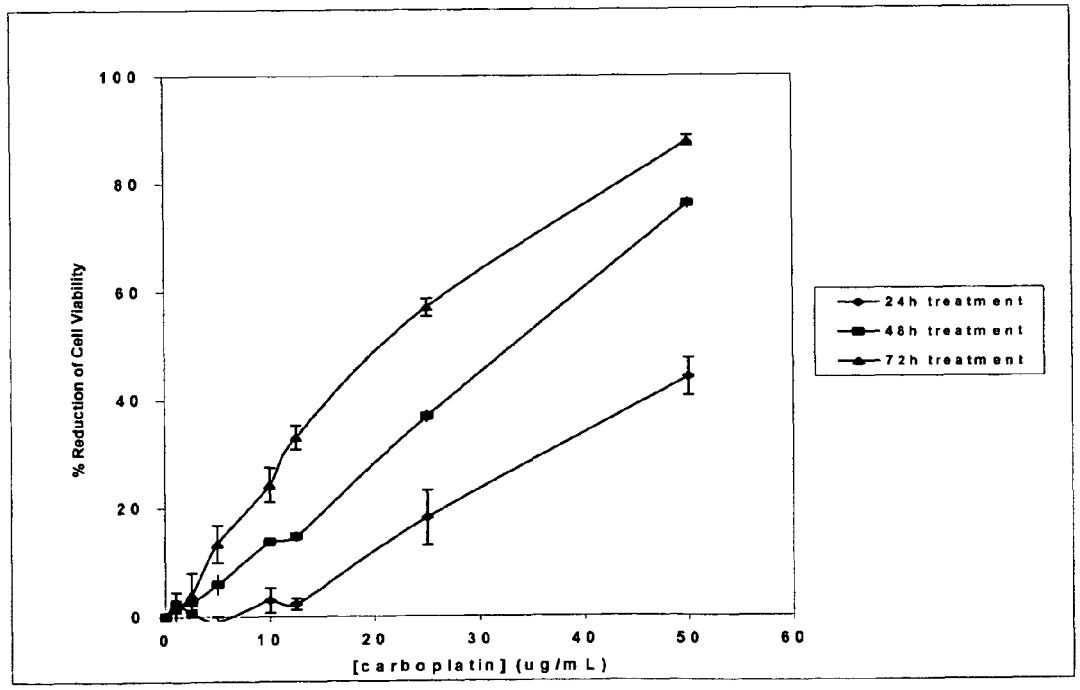
FIG. 6B. Enhanced chemosensitivity of SKOV3 ovarian cancer cells to sustained exposure to CPT.
Figure 8:
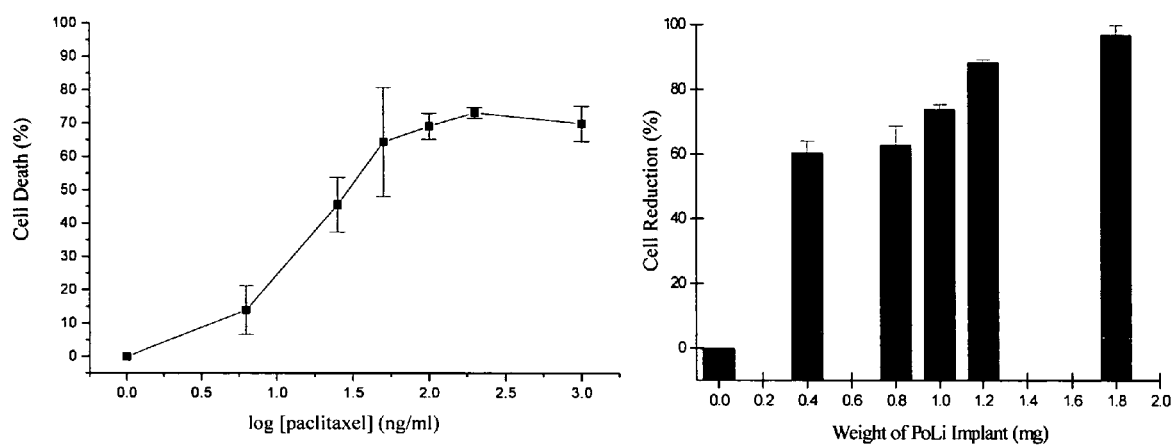
FIG. 8. The percent cell death of SKOV-3 human ovarian cancer cells with increasing concentrations of paclitaxel (a) and increasing amounts of the PoLi implant system (b) after 48 hours of incubation. The PoLi film contains 12 μg of paclitaxel per milligram of film.

In-vitro cytotoxicity studies in SKOV-3 cells were carried out in order to evaluate the biological activity of PTX loaded within the PoLi implant. SKOV-3 is a well characterized and established epithelial ovarian cancer cell line that is used routinely for screening cytotoxic agents [5]. The IC50 concentrations for free PTX in the SKOV-3 cell line was found to be 34.7 ng/ml following 48 hours of incubation (FIG. 8a). As shown in FIG. 6b the incubation of cells with implant containing no drug did not cause a reduction in cell proliferation. Implants of varying weights (0.4 mg-1.85 mg) containing 12 μg of PTX per milligram of implant were incubated with the SKOV-3 cells for 48 hours. The initial burst release of drug from the implant occurred during the sterilization procedure; thus, the expected release rate of drug during the 48 hours of incubation with cells is approximately 0.8% of total drug loaded per day.

In this way, the amount of drug released from the implant over the 48 hour period is approximately 0.08 μg, 0.16 μg, 0.19 μg, 0.24 μg and 0.35 μg for incubation with films weighing 0.4 mg, 0.8 mg, 1 mg, 1.25 mg and 1.85 mg respectively (FIG. 8b). By comparison, 0.050 μg of free PTX had a 64% reduction in cells while the implant that released 0.080 μg of PTX had a 60.5% reduction in SKOV-3 cells. Furthermore, 0.2 μg of free PTX had a 73% cell reduction, while a 0.19 μg release from implant had a 74% cell reduction. From this study it was concluded that the biological activity of PTX contained within the PoLi implant device is retained during film preparation, storage and incubation with SKOV-3 cells.

Example 11

In-Vivo Biocompatability of Implant

The biocompatibility of the PoLi implant was examined in vivo in healthy Balb/c mice. Balb/c mice were anesthetized and a 1 cm incision was made in the right lower quadrant of the abdomen under sterile conditions. PTX-loaded PoLi implants, CPT-loaded Poli implants and drug-free implants (50 mg, approximately 1 mm by 5 mm), which were previously sterilized using 80% ethanol, were inserted into the peritoneal cavity and the incision site sutured closed using 5-0 Silk Black braided sutures. Animals were returned to individual cages and allowed free access to food and water. Animals were monitored daily and incision sites were examined for signs of infection or inflammation. Animals were sacrificed at 2, 3 or 4 weeks after implantation of the PoLi implant (n=2/group) and examined post-mortem. The remaining PoLi implant was examined for signs of encapsulation and removed for further physical-chemical evaluations. The implantation site, peritoneal organs and peritoneal cavity were examined for signs of inflammation, infection or injury.

Figure 9:
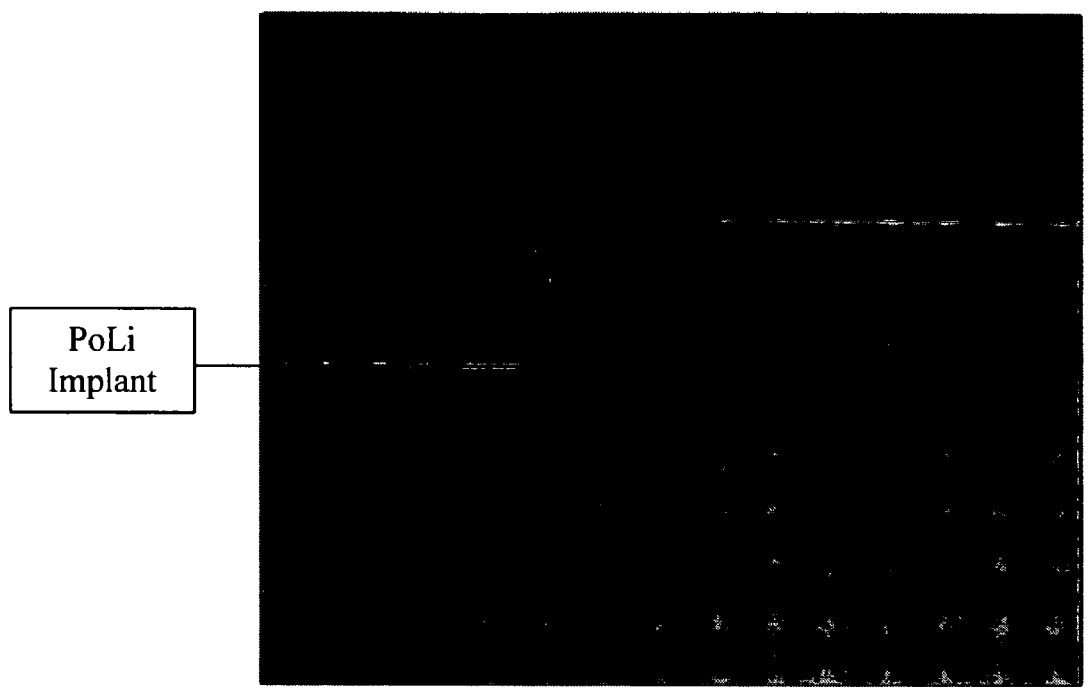
FIG. 9. Post-morteum examination of a male CD-1 mouse after one month of implantation of a paclitaxel loaded PoLi implant. No signs of internal inflammation, injury or infection were observed.

No signs of infection, inflammation or animal distress were seen in any of the animals implanted with either the PTX-loaded, the CPT-loaded or the drug-free PoLi implants. Post-mortem examination did not detect any signs of internal inflammation, injury or infection nor was there any evidence of implant encapsulation (FIG. 9). Scanning electron microscopy was performed on a PTX loaded PoLi implant prior to and following implantation in a CD-1 mouse after a one month period (FIG. 10). Most of the nanoparticles containing PTX were released from the surface of the PoLi implant.

Example 12

In Vivo Release of PTX and CPT from PTX-PoLi and CPT-PoLi Implants

Methods:

Drug release from the PTX-PoLi and CPT-PoLi systems was examined in vivo in healthy CD-1 mice. The CPT-PoLi system contained CPT nanoparticles loaded into the PoLi matrix at a drug:matrix ratio of 1:7. Two PTX-PoLi systems were examined, one containing a high PTX:matrix ratio (1:8) and another containing a low PTX:matrix ratio (1:67) system. CD-1 mice were anesthetized and a 1 cm incision was made in the right lower quadrant of the abdomen under sterile conditions. PTX-loaded PoLi implants and CPT-loaded Poli implants (50 mg, approximately 1 mm by 5 mm), which were previously sterilized using 80% ethanol, were inserted into the peritoneal cavity and the incision site sutured closed using 5-0 Silk Black braided sutures.

Animals were placed in metabolic cages continuously for the first 72 hours and then for 24 hour periods on Days 7 and 14 with free access to food and water. Total urine and fecal excretions were collected from the metabolic cages during the time intervals of 0-24 hr (Day 1), 24-48 hr (Day 2), 48-72 hr (Day 3), 144-168 hr (Day 7) and from 312-336 hr (Day 14). Urine and fecal excretions were measured, weighed and immediately frozen at −80° C. Samples were analyzed for total drug content as described below. Animals were housed in individual cages at all other time periods and monitored daily for symptoms of drug toxicity, infection or inflammation. Animals were sacrificed at 14 days after implantation of the PoLi implants (n=2/group) and examined post-morteum. The remaining PoLi implant was examined for signs of encapsulation and removed for further drug analysis and physical-chemical evaluations.

Concentrations of 14 [C]-PTX and its metabolites were measured by scintillation counting (Beckman LS5000TD, Beckman, Calif.). Amounts of total PTX collected in samples were calculated from standard curves prepared from 14 [C]-PTX spiked urine and fecal standards. Levels of 14 [C]-PTX in urine were below levels of detection. As fecal excretion accounts for 50% of the excretion of PTX and its metabolites in mice, the total amount of PTX excreted over each 24 hour interval was estimated from the amount collected in feces. For all drugs, once steady state is reached (after the first 24 hours), the rate of drug excretion is equal to the rate of drug input. Thus in vivo PTX release from the PoLi implant can be estimated by the rate of PTX appearance in feces, and this was calculated as follows:

(Total$\Sigma PTX$ released 24 hr=Total$\Sigma PTX$ excreted 24 hr=$\Sigma PTX$ feces 24 hr/0.5)

Concentrations of CPT and its metabolites were measured using inductively coupled plasma atomic emission spectrophotometry (ICP-AES) using previously described methods (J. Pharm. Biomed. Anal., 1990, 8, 1-30; Cancer 1998, 83, 930-935). The concentrations of CPT in samples was calculated from calibration curves generated from standards of CPT-spiked urine and fecal samples. CPT levels in fecal samples were negligible. As urinary excretion accounts for 90% of the excretion of CPT in mice, the total amount of CPT excreted over each 24 hour period was estimated from the amount collected in urine. For all drugs, once steady state is reached (after the first 24 hours), the rate of drug excretion is equal to the rate of drug input. Thus in vivo CPT release from the PoLi implant can be estimated by the rate of CPT appearance in urine, and this was calculated as follows:

(Total$\Sigma CPT$ released 24 hr=Total$\Sigma CPT$ 24 hr excreted=$\Sigma CPT$ urine 24 hr/0.9)

Figure 13:
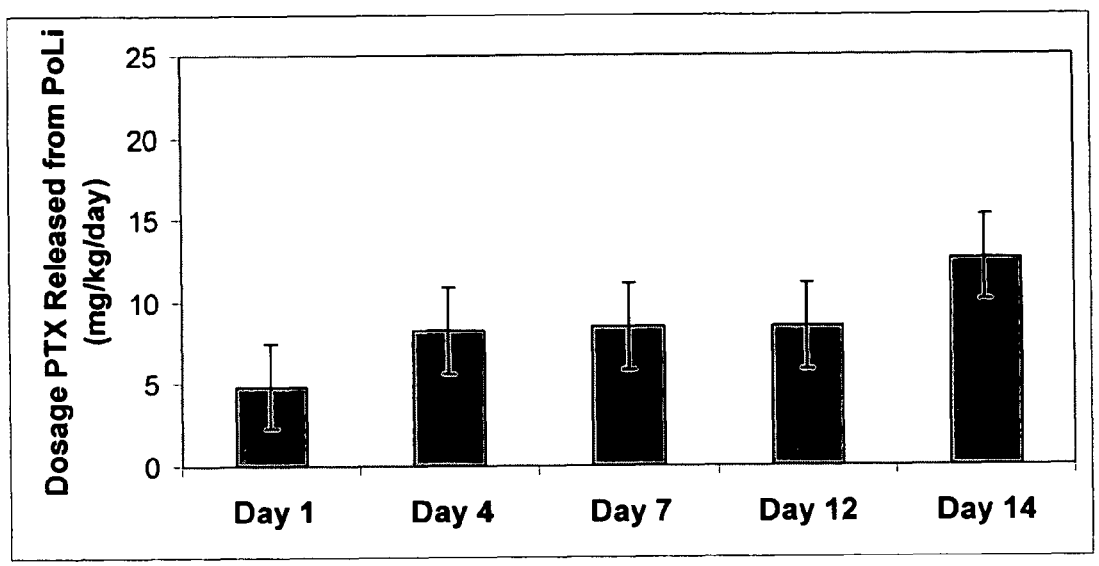
FIG. 13. Low Drug:Matrix PTX-PoLi Implant. Daily PTX dose provided from PTX PoLi delivery system implanted in vivo into peritoneal cavity of CD-1 mice. Data reported as mean±standard deviation.
Figure 14:
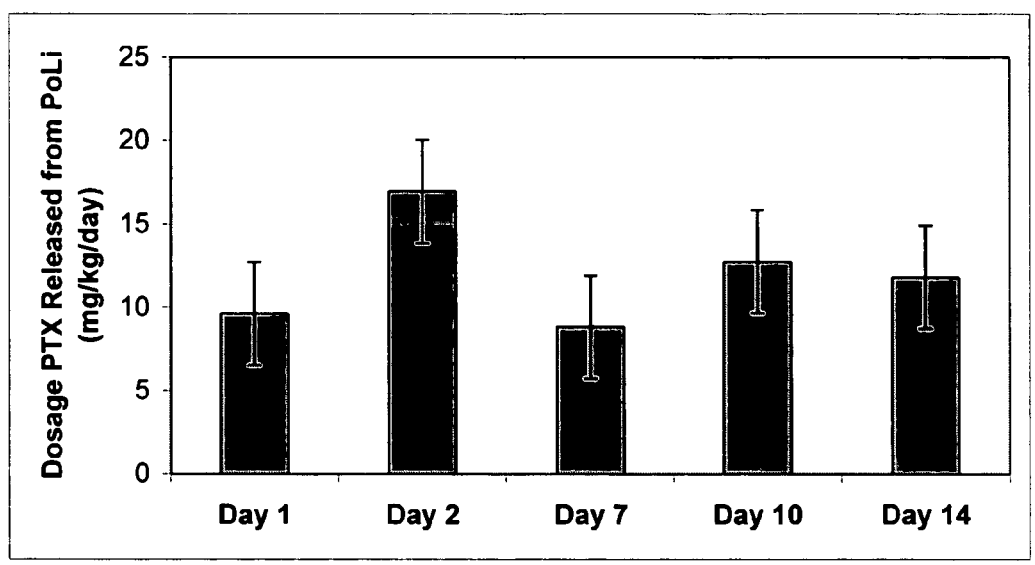
FIG. 14. High Drug:Matrix PTX:PoLi Implant. Daily PTX Dose provided from PTX PoLi delivery system implanted in vivo into peritoneal cavity of CD-1 mice. Data reported as mean±standard deviation.

Results of the in vivo release of PTX in fecal matter demonstrated a constant release of PTX from both the high drug:matrix and low drug:matrix system. Based on data generated from days 2 to 14 (steady state), the low drug:matrix system provided a constant release of 1±0.2 mg/kg/day (FIG. 13) while the high drug:matrix system provided a constant release of 0.65±0.2 mg/kg/day (FIG. 14) from the PTX-PoLi implants. In the first 24 hours a total of 6±3 µg and 25±5 µg were collected in the feces of mice implanted with the high and low drug:matrix implants, respectively. This is consistent with the drug collection and release seen over the following 14 days, suggesting that there is no initial in vivo burst release of PTX from the PoLi implant.

Figure 15:
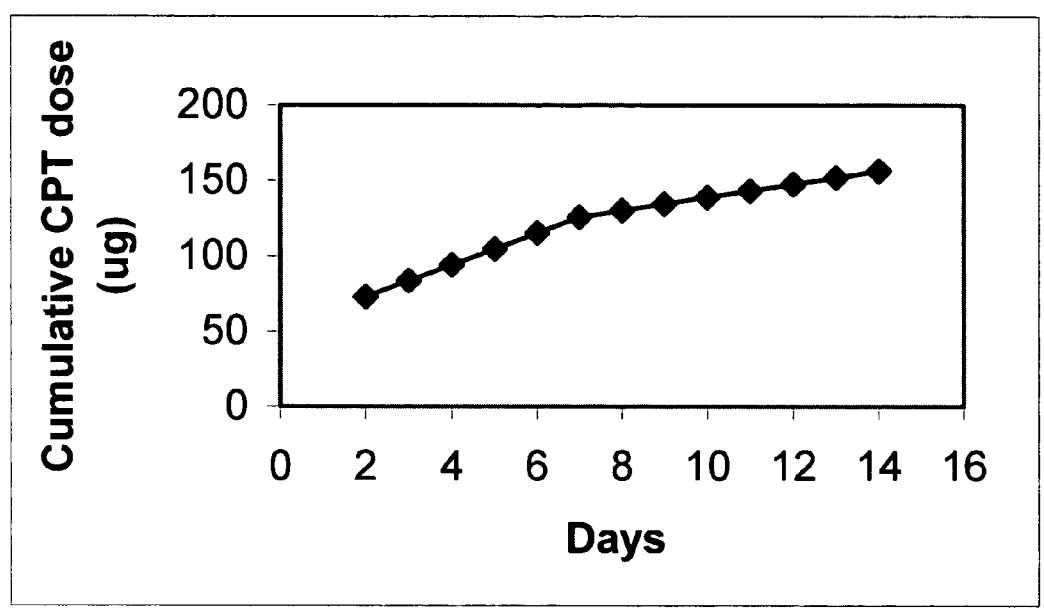
FIG. 15. CPT-PoLi Implant. Cumulative CPT Dose Provided from CPT PoLi delivery system implanted in vivo into peritoneal cavity of CD-1 mice. Data reported as average values based on urinary excretion of CPT.

In vivo excretion of CPT in urine demonstrated a constant release of CPT from the PoLi system. Our estimations from 24 to 72 hours (steady state), indicated that the CPT-PoLi implant provided a daily dose of 0.37±0.03 mg/kg/day and the daily dose released over 14 days averaged 0.25±0.15 mg/kg/day (FIG. 15). The initial release of CPT from the PoLi implant system provided a loading dose of approximately 72 µg CPT within the first 24 hours. No signs of drug toxicity, infection, inflammation or animal distress were seen in any of the animals implanted with either the PTX-loaded or CPT-loaded PoLi implants. Post-morteum examination did not detect any signs of internal inflammation, injury or infection nor was there any evidence of implant encapsulation.

Example 13

Demonstration of In Vitro Biocompatibility of PTX-Chitosan-ePC Implants

Cell viability and proliferation were examined in cells incubated with PTX-chitosan-ePC implants and cells incubated with drug-free chitosan-ePC implants. Cells were seeded onto 6-well culture plates and incubated with polymer implants (n=3/group) as described above. MTT was added to the cells at 0.5 mg/ml and incubated for 4 hrs at 37° C. Cells were then solubilized in 10% SDS. Formazan dye concentrations were then detected using a microplate reader (Gemini EM, Molecular Devices, Calif.) at an emission wavelength of 570 nm. Efficacy was expressed as the percent reduction in cell viability, which is the percentage of non-viable cells in relation to the untreated cells (control) set at 0% reduction in cell viability.

Cell appearance and morphology was examined using an inverted high-quality transmission light microscope (Zeiss Axiovert 135 TV; Zeiss, Oberkochen, Germany). Cells were incubated with drug-free chitosan-ePC implants of increasing sizes. No morphological changes were seen in SKOV-3 cells incubated with drug-free chitosan-ePC implants of increasing sizes (0.25-4.8 mg; 2.6-63.9 mm2) in comparison to untreated cells (FIG. 7). Cell toxicity was examined by looking at cell proliferation and viability using MTT assay. No significant reduction in cell proliferation or viability was detected in cells incubated with drug-free chitosan-ePC films in comparison to cells incubated without films. Hence, chitosan-ePC implants demonstrated in vitro biocompatibility.

Example 14

Demonstration of In Vitro Release and Cellular Uptake of PTX from the PTX-Chitosan-ePC Film Preparation of drug-free chitosan-ePC implant system and 14C-PTX-containing chitosan-ePC implant system (PTX-chitosan-ePC) containing a high PTX:matrix ratio (1:8) or low PTX:matrix ratio (1:67) are described elsewhere (Grant et al., J. Pharm. Sci. (2004)). In brief, a 2% (w/w) chitosan solution was prepared in 20 ml of distilled water containing 1% (v/v) acetic acid. EPC was dissolved in ethanol, blended with chitosan (such that ePC: chitosan ratio was 0.8:1 (w/w)) and PLGA nanoparticles containing 5 µCi of 14C-PTX (equivalent to 0.022 mg PTX) and 100 mg unlabeled PTX to make an implant of ~450 mg. The mixture was then homogenized (Polytron® PT-MR 3100, Kinematica A G), placed in a Teflon-coated dish and dried in a dessicator at room temperature. Implants were sterilized using 80% ethanol prior to use in in vitro and in vivo studies.

The human ovarian adenocarcinoma cell line, SKOV-3, obtained from the American Type Culture Collection (Maryland, USA), was maintained in RPMI 1640 supplemented with 10% FBS and 1% penicillin/streptomycin. The cells were grown at 37° C. in a humidified incubator equilibrated with 5% CO2. Medium was replaced three times a week and cells were trypsinized and subcultured every 5 days.

SKOV-3 cells were seeded onto 6-well plates with a total volume of 2 ml media per well. Once cells reached 80-90% confluency, sterilized implants of various sizes (0.25-4.8 mg; 2.6-63.9 mm2) were placed into each well. Each implant has a thickness of 0.15 mm and was cut into a square or rectangular shape. SKOV-3 cells were grown for 72 hrs in the presence of PTX-chitosan-ePC implants (0.25-4.8 mg implants containing 5.5×10-3–0.106 mg PTX) or drug-free chitosan-ePC implants (0.25-4.8 mg). At 72 hrs, media was collected and liquid scintillation counting (Beckman LS5000TD, Beckman, Calif.) was performed to detect the amounts of 14C-PTX released from implants. Cells were washed three times with 1× phosphate buffered saline (PBS) pH 7.4 and lysed with 1% triton. The cell lysate was collected and the amounts of 14C-PTX that accumulated inside the cells were counted using a liquid scintillation counter. PTX-chitosan-ePC implants were collected and dissolved in hydrogen peroxide overnight and amounts of PTX remaining in implants were also measured.

Figure 18:
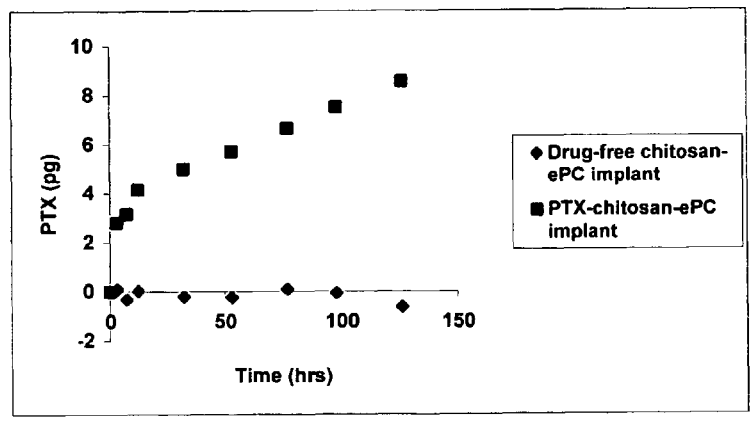
FIG. 18. A chart illustrating time course of cumulative amounts of 14C-PTX released into cell media from PTX-chitosan-ePC film (10 mg) incubated with SKOV-3 cells over 5 days.
Figure 19:
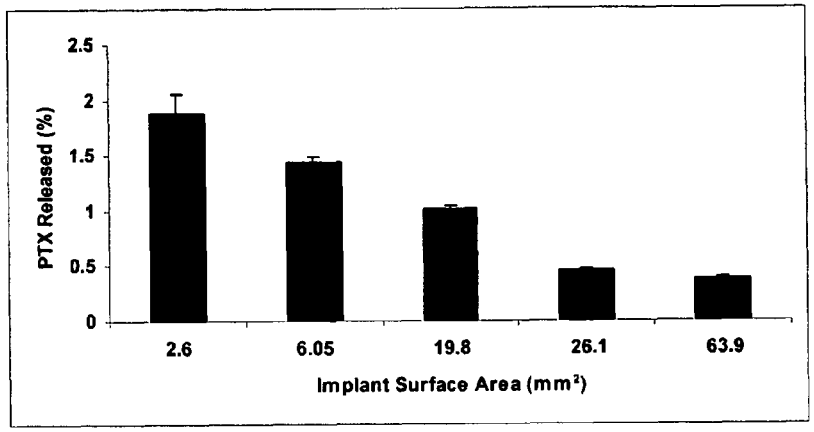
FIG. 19. A chart illustrating percentage of 14C-PTX released from PTX-chitosan-ePC implants of various sizes/surface areas in SKOV-3 cells after 72 hrs. Data represents the mean±S.D. (n=3).

The release rate of 14C-PTX from PTX-chitosan-ePC implants of a 10 mg size were studied in a tissue culture flask containing SKOV-3 cells in a total volume of 20 ml. Over a period of 5 days, 0.92±0.03 pg/day PTX was released from the implant with a cumulative dosage release of 8.55 pg PTX (FIG. 18). Initial burst release of PTX from the implant system was not detected. The release rates of various sized implants were also studied in 6-well plates. Interestingly, there was an inverse relationship between implant size and percentage of PTX released per day. More drug was released per day by smaller sized implants (1.88% per day) than larger implants (0.38% per day) (FIG. 19). This likely occurs due to the higher surface area of the smaller implants as well as the larger volume of media and ratio of media:implant in the cell wells.

Figure 20:
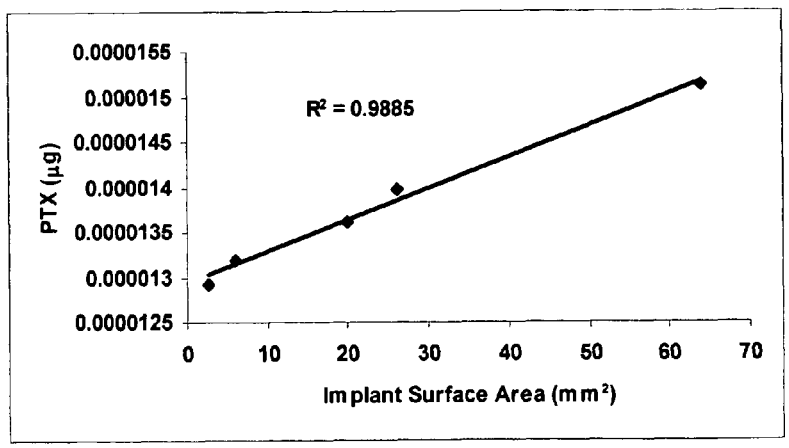
FIG. 20. A chart illustrating intracellular accumulation of 14C-PTX within SKOV-3 cells after 72 hrs of incubation with varying sizes (2.6-63.9 mm2) of PTX-chitosan-ePC. Data represents the mean±S.D. (n=3).

Increases in total drug released resulted in dose-dependent increases in the cellular uptake and intracellular accumulation of PTX (FIG. 20). Of note, it was found that the total sum of PTX released from the implant, accumulated in cells and remaining in implants after 72 hrs was equivalent to the total amount of PTX loaded in the implant (FIG. 16). This demonstrates that PTX loaded into the implant was not lost during handling and sterilization of the implant.

Example 15

Demonstration of in Vitro Efficacy of PTX-Chitosan-ePC Implants

Figure 17:
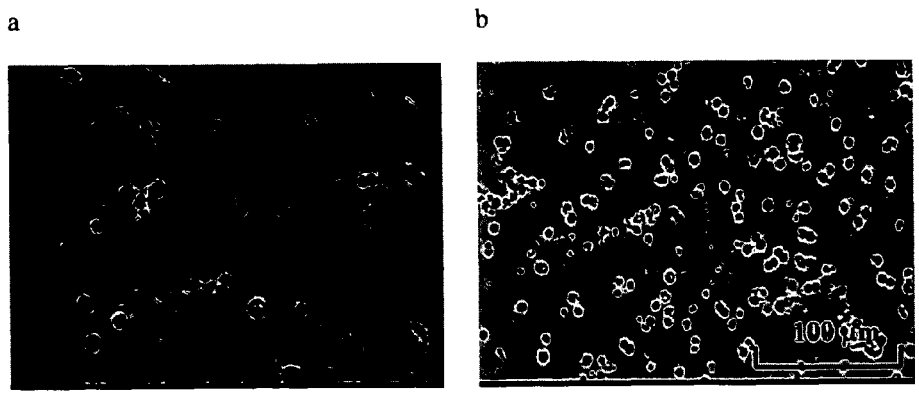
FIG. 17. A photograph illustrating SKOV-3 cell morphology and viability after 72 hrs of incubation with (a) drug free chitosan-ePC (4.8 mg; 63.9 mm2) (b) PTX-chitosan-ePC (4.8 mg; 63.9 mm2). Images obtained using the Zeiss Axiovert 135 TV light microscope at 10× magnification.

The cytotoxicity and anti-tumor effects of the PTX-chitosan-ePC implant was evaluated in vitro in human ovarian SKOV-3 cells using the MTT cytotoxicity assay. Incubation of PTX-chitosan-ePC implants (0.25-4.8 mg; 2.6-63.9 mm2) for 72 hrs were found to significantly decrease cell viability and proliferation in a dose-dependent manner (FIG. 17).

Figure 21:
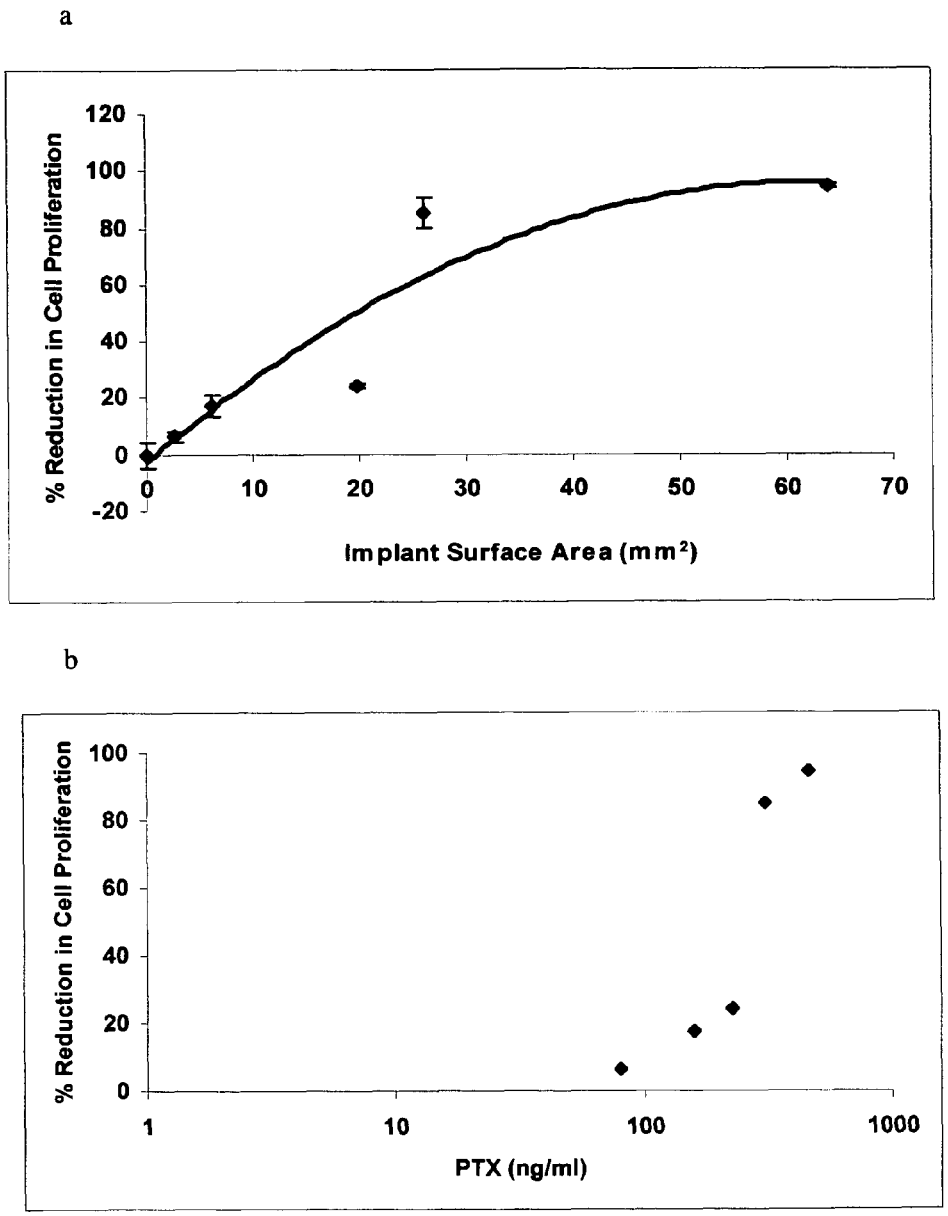
FIG. 21. A chart illustrating cell proliferation and viability of SKOV-3 cells incubated with various sizes of PTX-chitosan-ePC films for 72 hrs. PTX-chitosan-ePC dose is expressed as (a) implant surface area and (b) log concentration of PTX released into media. Data represents the mean±S.D. (n=3).

Increasing the size of implant, which results in a proportionate increase in dose, resulted in increased reduction in cell proliferation. The implant dose effective against 50% of the cells (ED50) was calculated to be 1.21 mg implant (0.211 µg/ml PTX). Maximal efficacy, with a reduction in cell proliferation of >90%, was seen with implants >2.5 mg (FIG. 21). This reveals that PTX released from the implants retained efficacy and activity in SKOV-3 cells.

Example 16

Demonstration of in Vivo Biocompatibility of Chitosan-ePC Implant

Biocompatibility and release studies of the chitosan-ePC implant were examined in vivo in healthy ten week old female CD-1 mice (25-35 g) (Charles River, St. Constant, QC) in accordance with the guidance of the Canadian Council on Animal Care. Each mouse was anesthetized and a 1 cm incision was made in the right lower quadrant of the abdomen under sterile conditions. Sterilized drug-free or PTX-chitosan-ePC implants (50 mg, approximately 1 mm by 5 mm with a thickness of 0.15 mm) were inserted into the peritoneal cavity and the incision site sutured closed. To study biocompatibility, animals containing drug-free chitosan-ePC implants were sacrificed at 2, 3 or 4 weeks after implantation (n=3/group) and examined post-mortem. The remaining chitosan-ePC implant was examined for signs of encapsulation and removed for further physico-chemical evaluations.

For in vivo release studies, animals implanted with drug-free or PTX-chitosan-ePC implants were placed in metabolic cages continuously for the first 72 hours and then for 24 hour periods on days 7 and 14 with free access to food and water. Total urine and fecal excretions were collected from the metabolic cages during the time intervals of 0-24 hr (Day 1), 24-48 hr (Day 2), 48-72 hr (Day 3), 144-168 hr (Day 7) and from 312-336 hr (Day 14). Urine and fecal excretions were measured, weighed and immediately frozen at −80° C. Samples were analyzed for total drug content as described below. Animals were housed in individual cages at all other time periods and monitored daily for symptoms of drug toxicity, infection or inflammation.

Animals were sacrificed at 14 or 28 days after implantation of the chitosan-ePC implants (n=3/group) and examined post-mortem. The implantation site, peritoneal organs and peritoneal cavity were examined for signs of inflammation, infection or injury. The remaining chitosan-ePC implant was examined for signs of encapsulation and removed for further analysis. Implants and surrounding capsid tissue (if present) were surgically removed and fixed in 4% paraformaldahyde. Specimens were paraffin embedded; 5 µm sections were cut and stained with hematoxylin and eosin (H&E). Slides were examined using Zeiss Axiovert 135 TV light microscope at 5× magnification.

Concentrations of 14 [C]-PTX and its metabolites were measured in feces and urine samples by scintillation counting. Amounts of total PTX collected in samples were calculated from standard curves prepared from 14C-PTX spiked urine and fecal standards. Levels of 14C-PTX in urine were below levels of detection. As fecal excretion accounts for 50% of the excretion of PTX and its metabolites in mice, the total amount of PTX excreted over each 24 hour interval was estimated from the amount collected in feces. Once steady state is reached (after the first 24 hours), the rate of drug input (drug released from implant) can be estimated from drug excretion (input=output). Thus in vivo PTX release from the chitosan-ePC implant was estimated by the rate of PTX appearance in feces, and this was calculated as follows:

(Total$\Sigma PTX$ released 24 hr=Total$\Sigma PTX$ excreted 24 hr=$\Sigma PTX$ in feces 24 hr/0.5)

Figure 22:
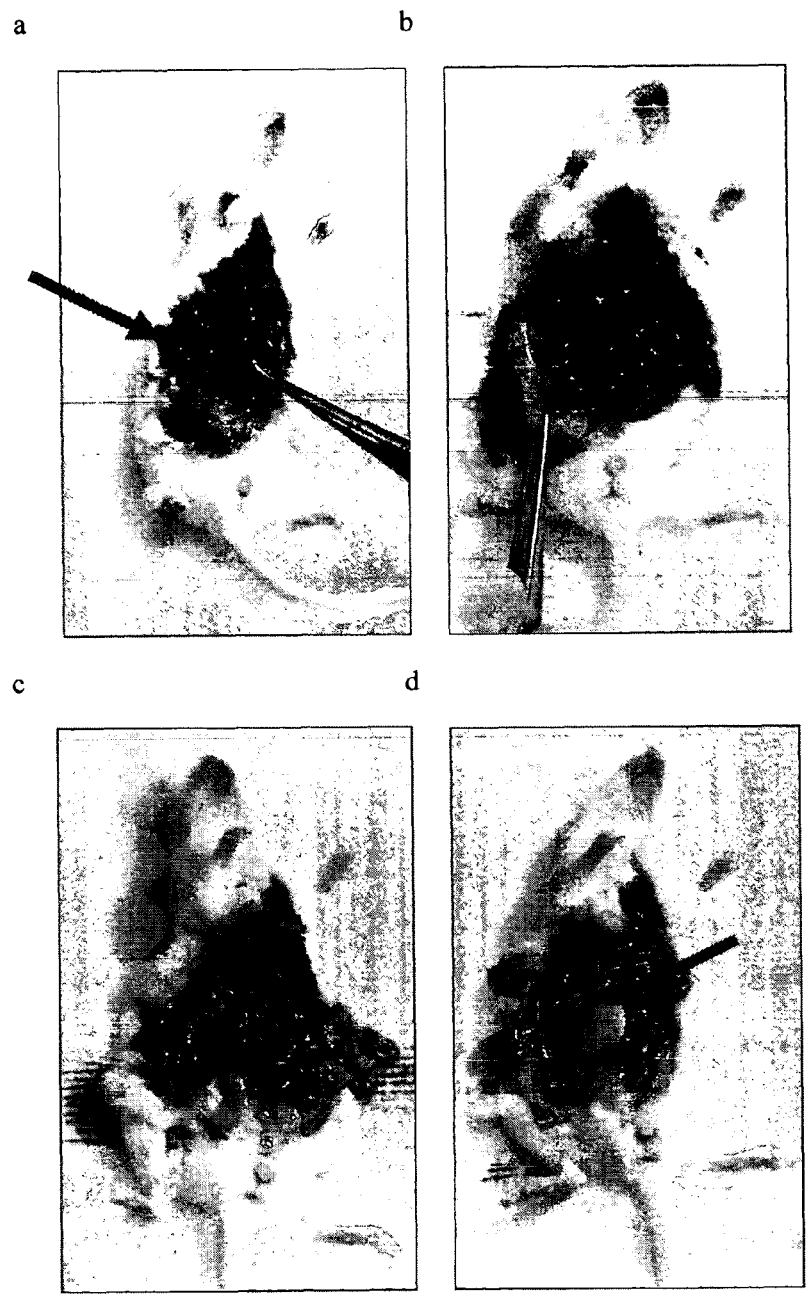
FIG. 22. Photographs illustrating post-mortem inspection and collection of different types of polymer films removed from animals 2 weeks after intraperitoneal implantation. (a) drug-free chitosan-ePC implant (b) drug-free PCL implant (c) drug-free PLA implant (d) PTX-chitosan-ePC implant.

No observable signs of inflammation, infection or distress were seen in any of the animals implanted with the PTX-chitosan-ePC system for 2 weeks or the drug-free chitosan-ePC implant after one month. Post-mortem visual examination did not detect any signs of internal inflammation, injury or infection nor were there any evidence of implant encapsulation in animals implanted with drug-free or PTX-chitosan-ePC (FIG. 22). In contrast, animals implanted with drug-free polycaprolactone (PCL) or drug-free poly(d,l-lactide) (PLA) implants displayed significant fibrous encapsulation surrounding the implant area (FIG. 22). Hematoxylin and eosin staining of the implants and its surrounding encapsulation (if any) allowed us to observe the extent of inflammation and fibrosis produced by the implants (FIG. 23). Pictures obtained for the PTX-chitosan-ePC (FIG. 23) and drug-free-chitosan-ePC (FIG. 23) implants clearly display no signs of protein adherence or fibrous encapsulation around the implants, signifying absence of an overt inflammatory response. In contrast, drug-free PCL (FIG. 23) and drug-free PLA (FIG. 23) implants displayed a greater degree of implant degradation with the induction of an inflammatory response resulting in fibrous encapsulation around the implant and its surrounding area. These results indicate that the chitosan-ePC implant system is biocompatible in vivo and its composition is suitable for the design of a novel drug delivery system.

Example 17

Demonstration of In Vivo Release of PTX from Chitosan-ePC Implant

PTX-chitosan-ePC implants were incubated in RPMI 1640 cellular media containing 10% FBS at 37° C. in an incubator equilibrated with 5% $CO_2$ for a period of 2 weeks. The values were compared to values obtained from the in vivo studies. In vitro—in vivo correlation for the release of PTX from the PTX-chitosan-ePC implant system were determined using Microsoft® Excel 2002.

The pattern of PTX excretion from mice implanted with the PTX-chitosan-ePC implant demonstrated a sustained and continuous in vivo release of PTX, which was consistent with in vitro release. The high drug:matrix and low drug:matrix PTX-chitosan-ePC implants provided sustained, zero-order release rates of 10.97+2.14 mg/kg/day (5.35+0.24% per day) and 1.02+0.35 mg/kg/day (3.53+0.60% per day) over the 2 week period, respectively (FIG. 25). In vivo, the high drug:matrix chitosan-ePC implant displayed a higher release rate than the low drug:matrix implants. In vivo results also indicate a consistent pattern of drug excretion in mice suggesting both in vivo zero-order release and an absence of burst effect.

Correlations between the in vitro and in vivo release rates of PTX from the PTX-chitosan-ePC implant system demonstrated a significant and strong linear correlation ($R2=0.975$) between the in vitro and in vivo models (FIG. 26). This signifies that the in vitro model is a good representation of PTX release from the PTX-chitosan-ePC in vivo.

Example 18

In Vivo Efficacy of Chitosan-ePC Drug Delivery System

Nude CD-1 female mice, 4-6 weeks old (Charles River, St. Constant, QC), were utilized for the conduction of the studies. Animals were handled and housed in sterile conditions as per institutional guidelines; with standard chow diet and water ad libitum and maintained on an automatic 12-hour light cycle at 22-24° C. Mice were inoculated intraperitoneally (IP) with $1 \times 10^7$ SKOV-3 cells.

Treatment was commenced 5 days post SKOV-3 inoculation. Animals were separated into several groups (n=3, per group). Two control groups were established: no treatment and drug free chitosan e-PC implant. Three different sized PTX chitosan-ePC implants were utilized for the delivery of various PTX doses (20, 70, 140 mg/kg/week) and were surgically inserted into animals under sterile conditions. In addition, weekly bolus PTX injections (20 mg/kg/week) were administered to the last group of animals. When the end-point of the study was reached (Day 25), animals were sacrificed and cut open for visual inspection. Implants and tissues were collected.

Tumours developed in the control groups and none of the treatment groups displayed any visible tumours post treatment (FIG. 26).

Other variations and modifications of the invention are possible. All such modifications or variations are believed to be within the sphere and scope of the invention as defined by the claims appended hereto.

We claim:

1. A drug delivery composition comprising:
a cross-linked film comprising a mixture of:
(a) a phospholipid,
(b) a chitosan said chitosan physically cross-linked to said phospholipid, and
(c) at least one pharmaceutically active agent,
the at least one pharmaceutically active agent incorporated in the cross-linked film as randomly dispersed molecules for sustained release of the at least one pharmaceutically active agent from the cross-linked film wherein the chitosan to phospholipid ratio is from about 0.03:1 to 2.5:1 w/w.

2. A drug delivery composition as claimed in claim 1 wherein the phospholipid is selected from the group consisting of phosphatidylcholines, phosphatidylethanolamine, egg phosphatidylcholine and phosphatidylglycerol.

3. A drug delivery composition as claimed in claim 1 wherein the chitosan based material comprises 85% chitosan and 15% chitin.

4. A drug delivery composition as claimed in claim 1 wherein the at least one pharmaceutically active agent is hydrophilic.

5. A drug delivery composition as claimed in claim 4 wherein the at least one hydrophilic pharmaceutically active agent is carboplatin.

6. A drug delivery composition as claimed in claim 1 wherein the at least one pharmaceutically active agent is hydrophobic.

7. A drug delivery composition as claimed in claim 6 wherein the at least one hydrophobic pharmaceutically active agent is paclitaxel.

8. A drug delivery composition as claimed in claim 1 further comprising at least one additive, wherein the additive is selected from the group consisting of polymeric nanoparticles, liposomes and hydrophilic polymers.

9. A drug delivery composition as claimed in claim 8 wherein the nanoparticle is poly (dl-lactide) nanoparticle.

10. A drug delivery composition as claimed in claim 1 further comprising a second pharmaceutically active agent.

11. A drug delivery composition as claimed in claim 1, wherein the at least one pharmaceutically active agent is selected from the group consisting of Carmustine, Methotrexate, Carboplatin, Cisplatin, Oxaliplatin, 5-Fluorouracil, 5-Fluorouridine, Cytarabine, Leuprolide acetate, Cyclophosphamide, Vinorelbine, Pilocarpine, Paclitaxel, Mitomycin, Camptothecin, Doxorubicin, Daunorubicin or Docetaxol.

12. A drug delivery composition of claim 1 wherein the cross-linked film is sized and formulated for intraperitoneal, intraarticular, intraocular, intratumoral, perivascular, subcutaneous, intracranial, intramuscular, periophthalmic, inside an eyelid, intraoral, intranasal, intra-bladder, intravaginal, intraurethral, or intrarectal, implantation to a mammal.

13. A method of manufacturing an implantable cross-linked film for sustained release of at least one pharmaceutically active agent in a mammal, said cross-linked film consisting of a phospholipid, a chitosan and at least one pharmaceutically active agent, wherein the chitosan to phospholipid ratio is from about 0.03:1 to 2.5:1 w/w said method comprising:
(a) complexing a chitosan based material with a phospholipid to form a chitosan-phospholipid solution;
(b) adding to the solution the at least one pharmaceutically active agent; and
(c) drying the chitosan-lipid solution including the at least one pharmaceutically active agent under conditions suitable to form the cross-linked film thereby providing a drug delivery composition for the sustained release of the at least one pharmaceutically active agent.

14. A method of manufacturing a drug delivery composition for sustained release as claimed in claim 13 further comprising encapsulating the at least one pharmaceutically active agent within an additive.

15. A method of manufacturing a drug delivery composition for sustained release as claimed in claim 14 further comprising adding a pharmaceutical acceptable carrier having at least a second pharmaceutically active agent.

16. A method of manufacturing a drug delivery composition for sustained release as claimed in claim 13, wherein said cross-linked film is sized and formulated for intraperitoneal, intraarticular, intraocular, intratumoral, perivascular, subcutaneous, intracranial, intramuscular, periophthalmic, inside an eyelid, intraoral, intranasal, intra-bladder, intravaginal, intraurethral, or intrarectal implantation to a mammal.

17. A method of treating a form of cancer treatable by local administration of the at least one pharmaceutically active agent in a subject in need comprising providing the drug delivery composition of claim 1 and implanting said drug delivery composition within the subject, wherein the at least one pharmaceutically active agent is an anti-cancer agent specific for said form of cancer.

18. The method as claimed in claim 17, wherein said form of cancer treatable by local administration of the at least one pharmaceutically active agent is ovarian cancer and said pharmaceutically active agent is selected from the group consisting of paclitaxel, carboplatin and combination thereof.

19. A drug delivery composition as claimed in claim 1, wherein the drug delivery composition is formulated for regional therapy.

20. A drug delivery composition comprising:
a crossed-linked film comprising a mixture of:
(a) a phospholipid,
(b) a chitosan, said chitosan physically cross-linked to said phospholipid, wherein the chitosan to phospholipid ratio is from about 0.03:1 to 2.5:1 w/w and
(c) at least one pharmaceutically active agent, the at least one pharmaceutically active agent incorporated in the cross-linked film as randomly dispersed molecules the for sustained release of the at least one pharmaceutically active agent from the cross-linked film, wherein said cross-linked film is obtained by drying a solution of the phospholipid and the chitosan based material with the incorporated at least one pharmaceutically active agent under conditions suitable to form the cross-linked film.

21. A method of treating a form of cancer treatable by local administration of the at least one pharmaceutically active agent in a subject in need comprising providing the drug delivery composition of claim 20 and implanting said drug delivery composition within the subject, wherein the at least one pharmaceutically active agent is an anti-cancer agent specific for said form of cancer.

22. An implantable device comprising:
a cross-linked film comprising a mixture of:
(a) a phospholipid,
(b) a chitosan based material, said chitosan based material physically cross-linked to said phospholipid, wherein the chitosan to phospholipid ratio is from about 0.03:1 to 2.5:1 w/w and
(c) at least one pharmaceutically active agent,
wherein said device is configured to be implanted to a fixed location within a cavity of a subject and remain in that fixed location within the subject for the sustained release of the at least one pharmaceutically active agent in said subject.

23. The device of claim 22, wherein said device has a size larger than 1 mm in diameter.

24. The device of claim 22, wherein said device can be implanted in the subject for local or regional therapy of the subject.

25. The method of claim 21 wherein the locally treatable form of cancer is selected from the group consisting of prostate, breast, ovarian, bladder, brain, liver, gastric, head and neck.

26. A method of locally treating a subject in need comprising providing the drug delivery composition of claim 20 and implanting said drug delivery composition within the subject.

27. The method of claim 17 wherein the form of cancer treatable by local administration of the at least one pharmaceutically active agent is selected from the group consisting of prostate, breast, ovarian, bladder, brain, liver, gastric, head and neck.

28. A drug delivery composition consisting of
a cross-linked film capable of being stable in aqueous solution consisting of a mixture of:
(a) a phospholipid,
(b) a chitosan, said chitosan physically cross-linked to said phospholipid, wherein the chitosan to phospholipid ratio is from about 0.03:1 to 2.5:1 w/w and
(c) at least one pharmaceutically active agent,
the at least one pharmaceutically active agent incorporated in the cross-linked film as randomly dispersed molecules for sustained release of the at least one pharmaceutically active agent from the cross-linked film.

29. The drug delivery composition of claim 27, wherein said cross-linked film is obtained by drying a solution of the phospholipid and the chitosan based material with the incorporated at least one pharmaceutically active agent under conditions suitable to form the cross-linked film.

30. An implantable device consisting of:
a cross-linked film consisting of a mixture of:
(a) a phospholipid,
(b) a chitosan, said chitosan physically cross-linked to said phospholipid, wherein the chitosan to phospholipid ratio is from about 0.03:1 to 2.5:1 w/w and
(c) at least one pharmaceutically active agent,
wherein said device is configured to be implanted to a fixed location within a cavity of a subject and remain in that fixed location within the subject for the sustained release of the at least one pharmaceutically active agent in said subject.

31. The drug delivery composition of claim 1, wherein said cross-linked film has a maximum swelling ratio of about 1.3 to about 43.8.

32. The drug delivery composition of claim 20, wherein said cross-linked film has a maximum swelling ratio of about 1.3 to about 43.8.

33. The implantable device of claim 22 wherein said device has a maximum swelling ratio of about 1.3 to about 43.8.

* * * * *